(12) United States Patent
Lautenschuetz et al.

(10) Patent No.: US 12,331,009 B2
(45) Date of Patent: Jun. 17, 2025

(54) CATALYST FOR THE SYNTHESIS OF ALKYL MERCAPTAN AND PROCESS FOR ITS PREPARATION

(71) Applicant: Evonik Operations GmbH, Essen (DE)

(72) Inventors: Ludger Lautenschuetz, Hanau (DE); Nadine Duerr, Alsbach (DE); Achim Fischer, Goldbach (DE); Manuel Weber-Stockbauer, Hohenau (DE); Oliver Yair Gutierrez-Tinoco, Richland, WA (US); Ricardo Bermejo Deval, Munich (DE); Johannes A. Lercher, Ottobrunn (DE)

(73) Assignee: Evonik Operations GmbH, Essen (DE)

( * ) Notice: Subject to any disclaimer, the term of this patent is extended or adjusted under 35 U.S.C. 154(b) by 603 days.

(21) Appl. No.: 17/425,907

(22) PCT Filed: Jan. 27, 2020

(86) PCT No.: PCT/EP2020/051903
§ 371 (c)(1),
(2) Date: Jul. 26, 2021

(87) PCT Pub. No.: WO2020/156992
PCT Pub. Date: Aug. 6, 2020

(65) Prior Publication Data
US 2022/0194896 A1 Jun. 23, 2022

(30) Foreign Application Priority Data
Jan. 29, 2019 (EP) .................................... 19154123

(51) Int. Cl.
| | | |
|---|---|---|
| C07C 319/08 | (2006.01) | |
| B01J 21/06 | (2006.01) | |
| B01J 23/04 | (2006.01) | |
| B01J 35/30 | (2024.01) | |
| B01J 37/00 | (2006.01) | |
| B01J 37/02 | (2006.01) | |
| B01J 37/08 | (2006.01) | |

(52) U.S. Cl.
CPC .......... C07C 319/08 (2013.01); B01J 21/063 (2013.01); B01J 21/066 (2013.01); B01J 23/04 (2013.01); B01J 35/397 (2024.01); B01J 37/0009 (2013.01); B01J 37/0203 (2013.01); B01J 37/082 (2013.01)

(58) Field of Classification Search
CPC ..... C07C 319/08; B01J 21/063; B01J 21/066; B01J 23/04; B01J 35/008; B01J 37/0203; B01J 27/04; B01J 35/002; B01J 37/0201; B01J 37/20
See application file for complete search history.

(56) References Cited

U.S. PATENT DOCUMENTS

| | | | | |
|---|---|---|---|---|
| 2,685,605 A | * | 8/1954 | Bell | C07C 321/00 568/71 |
| 2,820,060 A | * | 1/1958 | Miller | B01J 23/04 568/71 |
| 2,820,062 A | | 1/1958 | Folkins et al. | |
| 3,053,902 A | * | 9/1962 | Doumani | C07C 319/08 568/71 |
| 3,697,602 A | * | 10/1972 | Schreyer | C07C 319/08 568/71 |
| 4,950,763 A | | 8/1990 | Schommer et al. | |
| 5,852,219 A | | 12/1998 | Sauer et al. | |
| 5,874,630 A | | 2/1999 | Cook et al. | |
| 7,704,483 B2 | * | 4/2010 | Shen | C01G 25/02 423/594.12 |
| 8,022,254 B2 | * | 9/2011 | Redlingshofer | B01J 37/0215 502/305 |
| 8,609,576 B2 | * | 12/2013 | Redlingshoefer | B01J 37/0201 502/317 |
| 2005/0080295 A1 | | 4/2005 | Redlingshofer et al. | |
| 2009/0306432 A1 | | 12/2009 | Redlingshofer et al. | |
| 2010/0094059 A1 | | 4/2010 | Yang et al. | |

(Continued)

FOREIGN PATENT DOCUMENTS

| | | | | |
|---|---|---|---|---|
| CA | 1331004 | * | 7/1994 | ............ C07C 45/41 |
| CN | 101646649 A | | 2/2010 | |
| EP | 0 352 674 A2 | | 1/1990 | |
| GB | 2491698 A | * | 12/2012 | ............ B01J 21/063 |
| JP | 2005262184 A | | 9/2005 | |
| JP | 2016216360 A | | 12/2016 | |
| WO | WO 2005/021491 A1 | | 3/2005 | |
| WO | WO 2015/099053 A1 | | 7/2015 | |
| WO | WO 2017/114858 A1 | | 7/2017 | |

OTHER PUBLICATIONS

The Encyclopaedia Britannica (Encyclopaedia Britannica, Aug. 2008, academic.eb.com/levels/collegiate/article/anatase/7380, Accessed May 24, 2024). (Year: 2008).*

(Continued)

Primary Examiner — Ana Z Muresan
(74) Attorney, Agent, or Firm — Oblon, McClelland, Maier & Neustadt, L.L.P.

(57) ABSTRACT

A catalyst may include a support and from 5 to 20 wt.-% of a promoter, based on the total weight of the catalyst, wherein the support may include titanium dioxide, zirconium dioxide, and/or a mixture thereof, and the promoter may be an alkali metal oxide. Processes for preparing such catalysts may include impregnating a support of titanium dioxide and/or zirconium dioxide with an aqueous solution including a preferably soluble alkali compound and calcining. Alkyl mercaptans may be prepared in the presence of such catalysts or catalysts obtained by such processes.

8 Claims, 12 Drawing Sheets

(56) References Cited

U.S. PATENT DOCUMENTS

| | | | |
|---|---|---|---|
| 2011/0015443 A1* | 1/2011 | Barth | .................... C07C 319/02 568/70 |
| 2014/0158942 A1 | 6/2014 | Abbott et al. | |
| 2014/0357897 A1 | 12/2014 | Fonfe et al. | |

OTHER PUBLICATIONS

Extended European Search Report issued Jul. 16, 2019 in European Patent Application No. 19154123.4, 7 pages.

International Search Report and Written Opinion issued Apr. 7, 2020 in PCT/EP2020/051903 filed Jan. 27, 2020.

\* cited by examiner

CATALYST FOR THE SYNTHESIS OF ALKYL MERCAPTAN AND PROCESS FOR ITS PREPARATION

CROSS-REFERENCE TO RELATED APPLICATIONS

The present application is the national stage of international application PCT/EP2020/051903, filed on Jan. 27, 2020, and claims the benefit of the filing date of European Appl. No. 19154123.4, filed on Jan. 29, 2019.

The present invention relates to a $TiO_2$ and/or $ZrO_2$-based catalyst for the preparation of an alkyl mercaptan, and a process for its preparation. The present invention also relates to a process for preparing an alkyl mercaptan by reacting an alkyl alcohol with hydrogen sulfide in the presence of the supported catalyst according to the present invention or in the presence of a catalyst obtained by the process for its preparation according to the present invention.

Alkyl mercaptans are industrially important intermediates for the preparation of products with a high economic value. In particular, methyl mercaptan ($CH_3SH$) is an industrially important intermediate, for example in the synthesis of methionine, dimethyl sulfoxide, dimethyl sulfone or methanesulfonic acid. A variety of different synthesis routes was developed in the past, e.g. the hydrogenation of carbonyl sulfide (COS) or carbon disulfide ($CS_2$), the thiolation of methanol with $CS_2$ in the presence and absence of $H_2$ and the thiolation of methanol with hydrogen sulfide ($H_2S$) as thiolation agent in the presence of a catalyst based on aluminum oxide. The latter process represents the current industrial state of the art process, which is usually carried out in the gas phase at temperatures in the range of from 300 to 500° C. and a pressure in the range of from 1 to 25 bar.

The reaction mixture thus obtained contains the desired product methyl mercaptan together with unreacted starting materials and by-products, for example dimethyl sulfide and dimethyl ether, and also gases which are inert in respect of the reaction, for example methane, carbon monoxide, hydrogen and nitrogen. Consequently, the methyl mercaptan formed has to be separated off from this reaction mixture.

The separation of methyl mercaptan from the gaseous reaction mixture is usually effected by condensation of the methyl mercaptan. Here, the energy consumption for cooling the reaction mixture is a large cost factor. For a good economics of the process, it is therefore necessary to a have a high conversion and also a high selectivity for the formation of methyl mercaptan in order to keep energy input and invest costs as low as possible.

An improvement in activity and selectivity is obtainable by increasing the molar ratio of hydrogen sulfide to methanol. Molar ratios of between 1 and 10 are conventionally used. However, a high molar ratio also means a high excess of the hydrogen sulfide in the reaction mixture and thus the need to circulate large quantities of gas. To reduce the energy input required for this, the ratio of hydrogen sulfide to methanol should therefore deviate from 1 only slightly.

For an increase in activity and selectivity, specific $Al_2O_3$-based catalysts have been designed. It is generally accepted that aluminum oxide, in particular $\gamma$-$Al_2O_3$, is in principle the catalyst for the thiolation of methanol to give methyl mercaptan. However, the activity of aluminumoxide is too high and thus the catalyzed reaction does not stop at the desired product methyl mercaptan. Rather, the very active aluminum oxide also catalyzes the further reaction of methyl mercaptan to dimethyl sulfide. Therefore, aluminum oxide is usually admixed with an alkali metal tungstate, for example potassium tungstate or cesium tungstate, to decrease its activity, which leads to an increase in the selectivity for the formation of methyl mercaptan and decreased selectivity for the formation of side-products, such as dimethyl sulfide. In the thus obtained catalysts, the aluminum oxide is also referred to as support or catalyst carrier and the alkali metal tungstate as promoter. The proportion of the tungstate, based on the total weight of the catalyst, is usually up to about 20 wt.-%, as described, for example, in the U.S. Pat. No. 2,820,062. The catalyst disclosed in this document gives good activities and selectivities in the production of alkane thiols at a reaction temperature of 400° C. and a molar ratio of hydrogen sulfide to alkyl alcohol of 2:1.

The proportion of the alkali metal tungstate in the catalyst can be increased to 25 wt.-% and more in a relatively complicated preparation process, which involves a multiple impregnation of the support material with a solution of the alkali metal tungstate. The U.S. Pat. No. 5,852,219 discloses the advantages of using cesium tungstate ($Cs_2WO_4$) as promoter instead of potassium tungstate ($K_2WO_4$). Thus, increased activity can be achieved with good selectivity at the same time. According to Mashkina et al. (React. Kinet. Catal. Lett., vol. 36, No. 1, 159-164 (1988) the best selectivity for the formation of alkyl mercaptan from alkyl alcohols and hydrogen sulfide is achieved with catalysts in which the alkali/tungsten ratio equals 2:1. Impregnating an aluminum oxide carrier with a solution containing cesium and tungsten in the stoichiometric ratio of 2:1, allows to achieve a promoter loading of up to 40 wt.-%, based on the total weight of the catalyst, as described in U.S. Pat. No. 5,852,219. Increasing the concentration of the alkali tungstate to 25 wt.-% or more leads to an increase in the selectivity for the formation of methyl mercaptan. However, the disadvantage is that at the same time the activity of the catalyst decreases.

Multiple impregnation of a support material with a solution comprising cesium and tungsten in a non-stoichiometric ratio of less than 2:1, as described in US Pat. Appl. No. 2009/306432 A1 allows to increase the loading of the catalyst with a promoter to values of 25 wt.-% or more, based on the total weight of the catalyst. Although the loading of the aluminum with the promoter can be increased to more than 35% by weight by use of a non-stoichiometric ratio of cesium and tungsten in the impregnation solution, there is no longer a significant increase in activity or selectivity with such high loadings. Particularly, activity and selectivity even decrease with loadings above 45% by weight, based on the total weight of the catalyst. It is a further disadvantage that the catalyst produced by a multiple impregnation process do not have a uniform distribution of cesium and tungsten throughout the catalyst body. However, it is considered necessary to have a uniform distribution of catalytically active components throughout the catalyst body in order to achieve a high activity and a high selectivity in catalyzed reactions.

US Pat. Appl. No. 2014/357897 A1 discloses catalysts with a uniform distribution of alkali metal and tungsten thought the shaped catalyst body. These catalysts are produced by mixing the support material with an oxidic tungsten material, such as tungstic acid, and at least one separate alkali metal compound, such as cesium hydroxide to give a catalyst mass, followed by shaping of said catalyst mass. The thus obtained catalysts have a loading with the promoter of 45 wt.-% or more, based on the total weight of the catalyst. This allows yield and selectivity for the formation of methyl mercaptan to be further enhanced. However, high yield and selectivity of the said catalysts do not last long, and therefore, they are not suitable for use in industrial processes.

WO 2017/114858 A1 discloses another process for the preparation of catalysts for the preparation of alkane thiols. This preparation process represents a combination of the common impregnation procedure and the mixing or shaping process of US Pat. Appl. No. 2014/357897 A1. The activity and the methyl mercaptan selectivity of the thus obtained catalysts are comparable to other catalysts. However, the rather complicated preparation process does not lead to a performance increase.

As described above, considerable efforts were made to improve activity and selectivity of the catalyst for methanol thiolation. However, it appears that the catalyst system does not allow any further improvements in the methanol thiolation. It was therefore a problem to be solved to provide an improved catalyst for the methanol thiolation which has an improved selectivity compared to the catalysts of the prior art.

Surprisingly, it was found that this problem is solved by the use of a catalyst support different from the support of the prior art. This particular catalyst support is loaded with an alkali metal oxide.

An object of the present invention is therefore a catalyst comprising or consisting of a support and from 5 to 20 wt.-% of a promoter, based on the total weight of the catalyst, wherein the support comprises or consists of titanium dioxide, zirconium dioxide, and/or a mixture thereof, and the promoter is an alkali metal oxide.

Deviations from the content of 5 to 20 wt.-% of a promoter, based on the total weight of the catalyst, are still within the scope of the present invention, provided that they still lead to the effects of the present invention.

According to the present invention the support of the catalyst comprises or consists titanium dioxide, zirconium dioxide, and/or a mixture thereof. Therefore, the support does not necessarily have to consist of the titanium dioxide, zirconium dioxide, and/or a mixture thereof. This considers the cases where the materials still contain binders, fillers or any other components from their production. However, independently thereof the major amount of the material should be titanium dioxide, 35 zirconium dioxide, and/or a mixture thereof. Preferably, the support of the catalyst comprises at least 50 wt.-%, in particular from 55 to 100 wt.-%, 60 to 100 wt.-%, 65 to 100 wt.-%, 70 to 100 wt.-%, 75 to 100 wt.-%, 80 to 100 wt.-%, 85 to 100 wt.-%, 90 to 100 wt.-% or 95 to 100 wt.-% of titanium dioxide, zirconium dioxide and/or mixtures thereof. In an extreme case, the support consists of titanium dioxide, zirconium dioxide, and/or a mixture thereof.

The support materials according to the present invention do not only differ from the supports of the prior art in their elemental composition but also structurally. They comprise or consist of a tetragonal phase. In contrast, the pure $\gamma$-$Al_2O_3$ as the support of the catalysts in the prior art has a cubic phase.

In an embodiment at least a part of the support of the catalyst according to the present invention has a tetragonal phase. Preferably, the support of the catalyst according to the present invention consists of a tetragonal phase.

The catalyst of the prior art typically contain an alkali metal tungstate as promoter. However, it was found that it does not necessarily need an alkali metal tungstate to provide a catalyst with the desired selectivity for the formation of an alkyl mercaptan in an alkyl alcohol thiolation reaction. Rather, it is already sufficient to use an alkali metal oxide as promoter. During the start-up phase of the catalyst, the alkali metal oxide is sulfided.

In principle, the present invention is not limited regarding the choice of a specific alkali metal for the promoter. The alkali metal can therefore be any known alkali metal, preferably, sodium, potassium, cesium or rubidium. However, cesium is the alkali metal that improves the selectivity of the catalyst the most.

In a further embodiment of the catalyst according to the present invention the alkali metal is therefore sodium, potassium, cesium or rubidium.

In another embodiment of the catalyst according to the present invention the promoter is cesium oxide.

The Cs loaded catalysts according to the present invention give a significant increase in methyl mercaptan selectivity, compared to the catalysts of the prior art. For the $ZrO_2$ based catalyst with a loading of 10 wt.-% Cs, the selectivity to methyl mercaptan increased to a range of from $S_{CH3SH,\ 300°\ C.}=99.9\%$ to $S_{CH3SH,\ 360°\ C.}=99.1\%$. The only side product found was dimethyl sulfide with a selectivity of from $S_{DMS,\ 300°\ C.}=0.1\%$ to $S_{DMS,\ 360°\ C.}=0.9\%$. Increasing Cs loading to 20 wt.-% led to an even higher selectivity between $S_{CH3SH,\ 300°\ C.}=99.9\%$ and $S_{CH3SH,\ 360°\ C.}=99.4\%$. Similar results were found for the $TiO_2$ based catalysts: With 10 wt.-% Cs, the selectivity for methyl mercaptan increased to a range between $S_{CH3SH,\ 300°\ C.}=99.9\%$ to $S_{CH3SH,\ 360°\ C.}=99.4\%$. Again, the only side found was dimethyl sulfide with a selectivity of from $S_{DMS,\ 300°\ C.}=0.1\%$ to $S_{DMS,\ 360°\ C.}=0.6\%$. Increasing Cs loading to 20 wt.-% again led to an even higher selectivity between $S_{CH3SH,\ 300°\ C.}=99.9\%$ and $S_{CH3SH,\ 360°\ C.}=99.5\%$. The methyl mercaptan selectivity achieved by catalyst according to the present invention is more than 2%, absolute, higher than the methyl mercaptan selectivity achieved by the catalysts of the prior art. By comparison, the best catalysts of WO 2013/092129 A1 give a methyl mercaptan selectivity of 97.9% at best.

The catalyst according to the present invention comprises from 5 to 20 wt.-% of the promoter, based on the total weight of the catalyst. In case the catalyst is a shell catalyst, the quantity of 5 to 20 wt.-% relates to the composition of the shell.

In principle, the catalyst according to the present invention is not limited with respect to its shape. In its simplest form, said catalyst is a supported catalyst, where the alkali metal in oxidized and/or sulfide form has been applied to a zirconium dioxide and/or titanium dioxide comprising support. In that case an aqueous impregnation solution comprising a compound with the alkali metal in oxidized and/or sulfide form is impregnated directly onto a support body to produce the catalyst in the form of a supported catalyst. The support body is not limited with respect to a specific size. For example, it can be present as a powder with a particle size of less than 1000 µm, less than 500 µm, up to 250 µm, such as from 125 to 250 µm, or up to 125 µm, such as from 25 to 125 µm, determined in wet dispersion by means of laser scattering according to the International Standard ISO 13320 (2009). The catalyst according to the present invention can therefore also be present in the form of extrudates or pellets, obtained by impregnation of the powderous support with an aqueous solution containing a compound comprising the alkali metal in oxidized and/or sulfide form, followed by drying and calcination, wherein the calcination converts the alkali metal in oxidized and/or sulfide form into the alkali metal oxide. The thus obtained catalytic mass is mixed with a binder and subjected to a shaping to provide the full catalyst. Typically, the thus obtained catalyst is subjected again to a calcination, in which any binders are burnt off, optionally followed by a tempering step at a temperature of from 100 to 200° C.

In a further embodiment the catalyst according to the present invention is a full catalyst.

When a core-shell catalyst is produced, the powderous support as mentioned above is impregnated with the aqueous solution containing the compound comprising the alkali metal in oxidized and/or sulfide form. The thus obtained mixture is optionally calcinated, mixed with a binder and applied onto an inert support core in the form of a sphere, made e.g. of a ceramic, followed by calcination and optionally tempering to give a core-shell catalyst.

In another embodiment the catalyst according to the present invention is a core-shell catalyst.

The catalyst according to the present invention only requires the presence of an alkali metal in oxidized and/or sulfide form on the support but not necessarily the presence of a compound with tungsten in oxidized form, such as tungstic acid or a tungstate. This also simplifies the preparation of the catalyst significantly compared to the processes of the prior art, where a specific ratio of alkali to tungsten had to be met.

Another object of the present invention is a process for the preparation of a catalyst according to the present invention, which comprises the steps of
 a) impregnating a support comprising or consisting of titanium dioxide, zirconium dioxide, and/or a mixture thereof with an aqueous solution comprising a soluble alkali metal compound to provide an impregnated support,
 b) drying the impregnated support obtained from step a), and
 c) calcinating the dried impregnated support obtained from step b) to provide the catalyst.

For the application of the impregnation solution onto the support, various impregnating techniques can be used, such as dip impregnation, spray impregnation, vacuum impregnation and pore volume impregnation. This also makes it possible for the impregnation to take place more than once. In the case of formed pieces, the selected impregnating method must enable the desired loading quantity of the promoter to be applied with good uniformity over the entire cross section of the formed pieces. The impregnation solution is preferably applied onto the formed pieces in one or two steps by spray or vacuum impregnation. In spray impregnation, the aqueous impregnating solution is sprayed onto the support bodies. In vacuum impregnation, reduced pressure is generated using a vacuum pump in a vessel filled with the formed pieces. By opening a connection to the aqueous impregnating solution, the solution is sucked into the vessel until the entire charge of formed pieces is covered with the solution. After an impregnating period of 0.2 to 2 hours, the solution not taken up by the material is discharged or poured off. By pre-drying for a period of 1 to 10 hours at room temperature, the initial concentration gradient over the cross section of the formed pieces can be largely equalized. Thus, the uniformity of the impregnation over the cross section of the catalyst particles is improved. The catalyst precursors thus obtained are preferably dried overnight, e.g. for a period of 1 to 10 hours at 50 to 100° C., preferably 60 to 80° C., to remove the residual moisture. A calcination then takes place for a period of 1 to 20 hours, preferably 1 to 5 hours at 300 to 600, preferably 420 to 480° C. As a result, the alkali metal in oxidized and/or sulfide form from the impregnation solution is transferred into the alkali metal oxide as promoter, said promoter is fixed on the support and the anion from the impregnating solution is destroyed and driven off. A gas stream may optionally flow through the charge of support bodies for the catalyst precursors during the drying and calcining, which improves the removal of the residual moisture and decomposition gases. Deviations from the explicitly mentioned values for the period and the temperature of the calcination are within the scope of the present invention, provided they lead to the same quality of effect as the explicitly mentioned values.

The process according to the present invention is not limited regarding the choice of the alkali metal compound in the impregnation solution. The only requirements are that the alkali metal compound must have a sufficient solubility in water in order to load the support with the desired concentration of the alkali metal, and that the anion easily decomposes during the calcination step. It is therefore preferred to use an alkali metal hydroxide, an alkali metal acetate, an alkali metal carbonate or an alkali metal nitrate.

Notwithstanding, it is also possible to use an alkali metal compound with a relatively low solubility in water. When the low solubility of an alkali metal compound in water does not allow to obtain the desired alkali metal loading in a single impregnation step, the impregnation of the support can also take place in multiple steps, particularly in two steps. For example, the impregnation solution used in the first step then contains one to two thirds of the total quantity of the compound comprising the alkali metal in oxidized and/or sulfide form and the remaining quantity is applied to the support in the second or any further step. In a multiple-step, e.g. a two-step procedure, the intermediate product obtained in the first step is optionally not calcinated. Apart from this, the same impregnation, drying and calcination program takes place in the second step as described for the one-step process.

In one embodiment of the process for the preparation of a catalyst according to the present invention the steps a) to b) or a) to c) are repeated at least once.

The catalyst thus obtained, in particular from step c) can be mixed with a binder and then subjected to shaping process, such as an extrudation or a pelletizing, to give a full catalyst. The thus obtained extrudates or pellets are subjected to a final calcination and optionally tempering.

In another embodiment the process for the preparation of a catalyst further comprises the step
 d1) shaping the catalyst obtained from step c) of the process for the preparation of a catalyst to give a full catalyst.

Alternatively, it is also possible to apply the catalyst from step c) to a core to give a core-shell catalyst. For this purpose, the catalyst obtained from step c) is suspended in a solvent, preferably in water, mixed with a binder and the thus obtained mixture is applied to an inert core, e.g. made of ceramic material, by e.g. spray-drying, followed by calcination to remove the solvent and to burn off the binder, and optionally tempering.

In an alternative embodiment the process for the preparation of a catalyst further comprises the step
 d2) applying the catalyst obtained from step c) of the process for the preparation of a catalyst to a core to provide a core-shell catalyst.

The catalysts according to the present invention as well as the catalysts obtained by the process according to the present invention are suitable for the catalyzed reaction of alkyl alcohols with hydrogen sulfide to give alkyl mercaptans, also known alkyl alcohol thiolation.

A further object of the present invention is therefore a process for the preparation of an alkyl mercaptan, wherein an alkyl alcohol is reacted with hydrogen sulfide in the presence of the catalyst according to the present invention or the catalyst obtained by the process according to the present invention.

In principle the thiolation process according to the present invention is not limited to the use of a particular alkyl alcohol or the preparation of a particular alkyl mercaptan. However, the economically most relevant alkyl alcohol is methyl mercaptan.

In an embodiment of the thiolation process according to the present invention the alkyl alcohol to be reacted is therefore methanol and the alkyl mercaptan to be prepared is methyl mercaptan.

The present invention is further illustrated by the following items:

1. A catalyst comprising a support and a promoter, wherein the support comprises titanium dioxide, zirconium dioxide, and/or a mixture thereof, and the promoter is an alkali metal in oxidized and/or sulfide form.
2. The catalyst according to item 1, wherein at least a part of the support has a tetragonal phase.
3. The catalyst according to item 1 or 2, wherein the promoter is an alkali metal oxide and/or alkali metal sulfide.
4. The catalyst according to any of items 1 to 3, wherein the alkali metal is sodium, potassium, cesium or rubidium.
5. The catalyst according to any of items 1 to 4, wherein the catalyst comprises up to 25 wt.-% of the promoter, based on the total weight of the catalyst.
6. The catalyst according to any of items 1 to 5, wherein the catalyst comprises from 5 to 20 wt.-% of the promoter, based on the total weight of the catalyst.
7. The catalyst according to any of items 1 to 6, wherein the promoter is cesium oxide and/or cesium sulfide and the catalyst comprises from 5 to 20 wt.-% of said promoter, based on the total weight of the catalyst.
8. The catalyst according to any of items 1 to 7, wherein the catalyst is a full catalyst.
9. The catalyst according to any of items 1 to 8, wherein the catalyst is a core-shell catalyst.
10. A process for the preparation of a supported catalyst according to any of items 1 to 7, comprising the steps of
    a) impregnating a support comprising titanium dioxide, zirconium dioxide, and/or a mixture thereof with an aqueous solution comprising a soluble alkali compound,
    b) drying the impregnated support obtained from step a), and
    c) calcinating the dried impregnated support of step b) to provide the catalyst.
11. The process according to item 10, wherein the steps a) to c) are repeated at least once.
12. The process according to item 10 or 11, further comprising the step
    d1) shaping the catalyst obtained from step c) to give a full catalyst.
13. The process according to item 10 or 11, further comprising the step
    d2) applying the catalyst obtained from step c) to a core to provide a core-shell catalyst.
14. A process for the preparation of an alkyl mercaptan, wherein an alkyl alcohol is reacted with hydrogen sulfide in the presence of the catalyst according to any of items 1 to 9 or the catalyst obtained by the process according to any of items 10 to 13.
15. The process according to item 14, wherein the alkyl alcohol to be reacted is methanol and the alkyl mercaptan to be prepared is methyl mercaptan.

EXAMPLES

Figure 1:
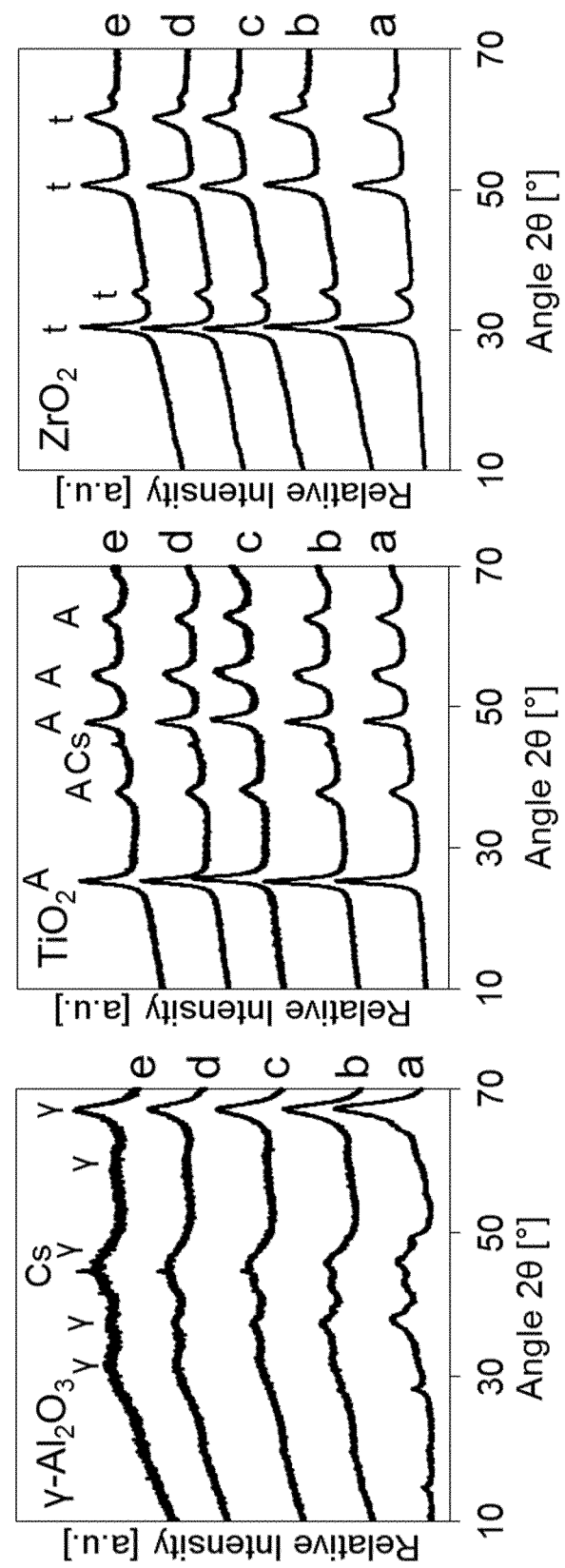
FIG. 1 shows the XRD patterns of pure metal oxides (a) and metal oxides loaded with 5 wt.-% Cs (b), 10 wt.-% Cs (c), 15 wt.-% Cs (d) and 20 wt.-% Cs (e), with γ indicating characteristic signals of pure γ-$Al_2O_3$, t indicating tetragonal $ZrO_2$, A indicating anatase ($TiO_2$) and Cs indicating $Cs_2CO_3$.

1. Preparation of Cs Loaded Metal Oxides According to the Invention

Catalysts with a Cs loading of 5, 10, 15 and 20 wt.-%, based on the total weight of the catalysts, were prepared by incipient wetness impregnation of the commercially available metal oxides γ-$Al_2O_3$ (Spheralite 101, Axens), $TiO_2$ (Hombikat 100 UV, Sachtleben), and $ZrO_2$ (SZ 61152, Norpro), each having grain sizes of 0.125-0.25 mm, with an aqueous solution of cesium acetate, added dropwise to the agitated solid. For each Cs loading different impregnation solutions were prepared containing the required amount of cesium acetate to provide the desired Cs loading. 76 mg of cesium acetate (Sigma Aldrich, >99.99%) were dissolved in 0.5 mL $H_2O$ per 1 g of support to give a Cs loading of 5 wt.-%, respectively 160.5 of cesium acetate for a Cs loading of 10 wt.-%, 255 mg of cesium acetate for a Cs loading of 15 wt.-%, and 361.0 mg of cesium acetate for a Cs loading of 20 wt.-%. The impregnated metal oxides were dried over night at 70° C., followed by calcination in flowing synthetic air with a flow rate of 100 mL/min and at 400° C. for 2 h, achieved with a temperature ramp of 0.5° C./min. Prior to their use in the catalytic testing, all samples were activated by treatment in $H_2S$ with a flow rate of 20 ml/min at 360° C. for 2 hours.

2. Characterization of the Prepared Catalysts 2.1 Elemental Composition and Surface Area Determination The elemental composition of the prepared catalysts according to the invention was determined by atomic absorption spectroscopy (AAS). The measurements were performed on an UNICAM 939 AA-Spectrometer. To determine the textural properties, $N_2$ physisorption was performed on a Porous Materials Inc. BET-121 sorptometer. After activation at 250° C. for 2 h under vacuum, $N_2$ was adsorbed at a temperature of 77.4 K. The surface area was calculated using the BET-method. The results for elemental analysis and surface determination of all prepared catalysts are summarized in table 1 below.

TABLE 1

Results for elemental analysis and surface determination for all prepared catalysts

| Support material | Determined parameter | Cs loading [wt.-%] | | | | |
|---|---|---|---|---|---|---|
| | | 0 | 5 | 10 | 15 | 20 |
| $Al_2O_3$ | c(Cs) [mmol $g^{-1}$] | 0 | 0.3 | 0.7 | 1.2 | 1.4 |
| $TiO_2$ | | 0 | 0.4 | 0.7 | 1.1 | 1.5 |
| $ZrO_2$ | | 0 | 0.4 | 0.8 | 1.1 | 1.5 |
| $Al_2O_3$ | $S_{BET}$ [$m^2$ $g^{-1}$] | 283 | 260 | 239 | 171 | 154 |
| $TiO_2$ | | 314 | 243 | 232 | 195 | 109 |
| $ZrO_2$ | | 126 | 123 | 70 | 62 | 50 |

The results show that comparable loadings with Cs were achieved for each of three types of support materials. In general, the specific surface area of the prepared supported catalysts decreases with increasing Cs loading. This can be attributed to the increased density of the catalyst and coverage of the surface with Cs, both leading to a loss in surface area.

The table 2 below summarizes the different masses of cesium acetate in the different impregnation solutions used in the preparation of the catalysts, the masses of $Cs^+$ in these impregnation solutions (the weight of the acetate counterion was neglected), the mass of the catalysts (support+$Cs^+$), the theoretical concentration ($C_{Th}$(M(cesium)/m(catalyst)) of $Cs^+$ in the prepared catalysts, and the concentration ($C_{EA}$(M(cesium)/m(catalyst)) of $Cs^+$ in the prepared catalysts found with elemental analysis.

TABLE 2

Overview over the prepared catalyst and their concentrations of cesium.

| Catalyst/ loading | m(CsAc) [g] | m($Cs^+$) [g] | m(cat) [g] | $C_{Th}$(Cs/Cat) [mmol/g] | $C_{EA}$(Cs/cat) [mmol/g] |
|---|---|---|---|---|---|
| Cs(5 wt.-%)/$ZrO_2$ | 0.076 | 0.052 | 1.052 | 0.38 | 0.4 |
| Cs(10 wt.-%)/$ZrO_2$ | 0.160 | 0.110 | 1.100 | 0.75 | 0.8 |
| Cs(15 wt.-%)/$ZrO_2$ | 0.255 | 0.175 | 1.175 | 1.13 | 1.1 |
| Cs(20 wt.-%)/$ZrO_2$ | 0.361 | 0.248 | 1.248 | 1.50 | 1.5 |
| Cs(5 wt.-%)/$TiO_2$ | 0.076 | 0.052 | 1.052 | 0.38 | 0.3 |
| Cs(10 wt.-%)/$TiO_2$ | 0.160 | 0.110 | 1.100 | 0.75 | 0.7 |
| Cs(15 wt.-%)/$TiO_2$ | 0.255 | 0.175 | 1.175 | 1.13 | 1.2 |
| Cs(20 wt.-%)/$TiO_2$ | 0.361 | 0.248 | 1.248 | 1.50 | 1.5 |
| Cs(5 wt.-%)/$Al_2O_3$ | 0.076 | 0.052 | 1.052 | 0.38 | 0.4 |
| Cs(10 wt.-%)/$Al_2O_3$ | 0.160 | 0.110 | 1.100 | 0.75 | 0.7 |
| Cs(15 wt.-%)/$Al_2O_3$ | 0.255 | 0.175 | 1.175 | 1.13 | 1.1 |
| Cs(20 wt.-%)/$Al_2O_3$ | 0.361 | 0.248 | 1.248 | 1.50 | 1.5 |

2.2 Crystal Structure

The crystalline structure of all support and all catalysts was determined by powder X-ray diffraction. XRD patterns were collected with a Philips X'Pert System (Cu Kα radiation, 0.1542 nm) operating at 45 kV/40 mA, using a nickel Kβ-filter and solid-state detector (X'Celerator). The measurements were carried out with a step size of 0.0170 and scan time of 0.31 s per step.

The support materials gave the expected diffraction patterns, being phase-pure in γ-$Al_2O_3$, anatase in $TiO_2$, and tetragonal zirconia in $ZrO_2$. The XRD patterns are shown in FIG. 1. Upon Cs addition there was no change in the crystal structure of the support material, showing the same diffraction pattern. An additional diffraction peak was observed on γ-$Al_2O_3$ and $TiO_2$ at 45° C., indicative of $Cs_2CO_3$. The carbonate is believed to be formed by the reaction of the surface Cs species with atmospheric $CO_2$. Upon sulfidation, the carbonate and its peaks disappeared leading to the formation of sulfur oxyanions, that were not detected by means of X-ray diffraction. No other reflections appeared. It is therefore concluded that the active Cs species is XRD amorphous.

2.3 Characterization of Acid Base Properties

Adsorption of CO and pyridine onto the pure metal oxides and the prepared catalysts was monitored via IR spectroscopy in transmission absorption mode (samples pressed into self-supporting wafers) to measure the Lewis acidity. Before the adsorption, the samples were heated to 360° C. with a hating ramp of 10° C. per minute under a helium flow of 10 mL per minute. Subsequently, the samples were sulfided for 0.5 h at 360° C. under a flow of 10 mL per minute of 10 vol.-% of hydrogen sulfide in nitrogen. To remove physisorbed hydrogen sulfide, the sample was flushed with a He flow of 10 mL per minute for another 15 min, before it was evacuated to $10^{-7}$ mbar and cooled down to 50° C. For pyridine adsorption, the cell was cooled down to 50° C. and the sample was exposed to pyridine at a partial pressure of 1 mbar of pyridine, followed by decreasing the pyridine partial pressure. Further evacuation to $10^{-5}$ mbar resulted in no pyridine adsorbed on Cs containing samples. Thus, spectra from different catalysts were compared at 0.1 mbar, before evacuation took place. The concentrations of coordinating pyridine were calculated using the molar integrated extinction coefficient of 0.96 cm per μmol determined for the characteristic band at 1450 $cm^{-1}$. CO adsorption took place by cooling down the IR cell to −150° C., using liquid nitrogen. The spectra were recorded at a CO partial pressure of 5 mbar.

Methanol was adsorbed at 50° C., while stepwise increasing the methanol partial pressure (0.1 mbar, 0.5 mbar, 1 mbar and 5 mbar) followed by an increase in temperature to 300° C. All spectra were recorded with a Nicolet 6700 FTIR spectrometer (64 scans were collected to obtain each spectrum). All spectra were subjected to a background subtraction and normalized to the mass of the wafer.

2.4 Pyridine Absorption

Figure 2:
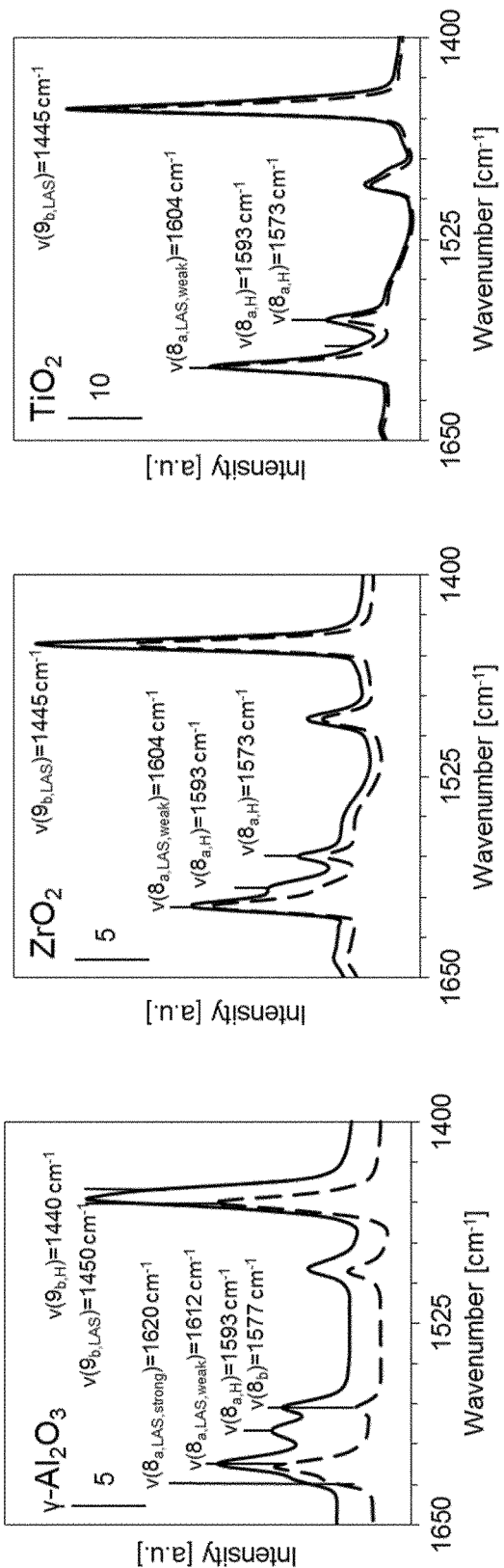
FIG. 2 shows the subtracted IR spectra of absorbed pyridine on the pure metal oxides at 50° C., with the solid line representing the IR spectrum taken a pyridine partial pressure of 0.1 mbar and the broken line representing the IR spectrum taken after evacuation at $10^{-7}$ mbar.
Figure 3:
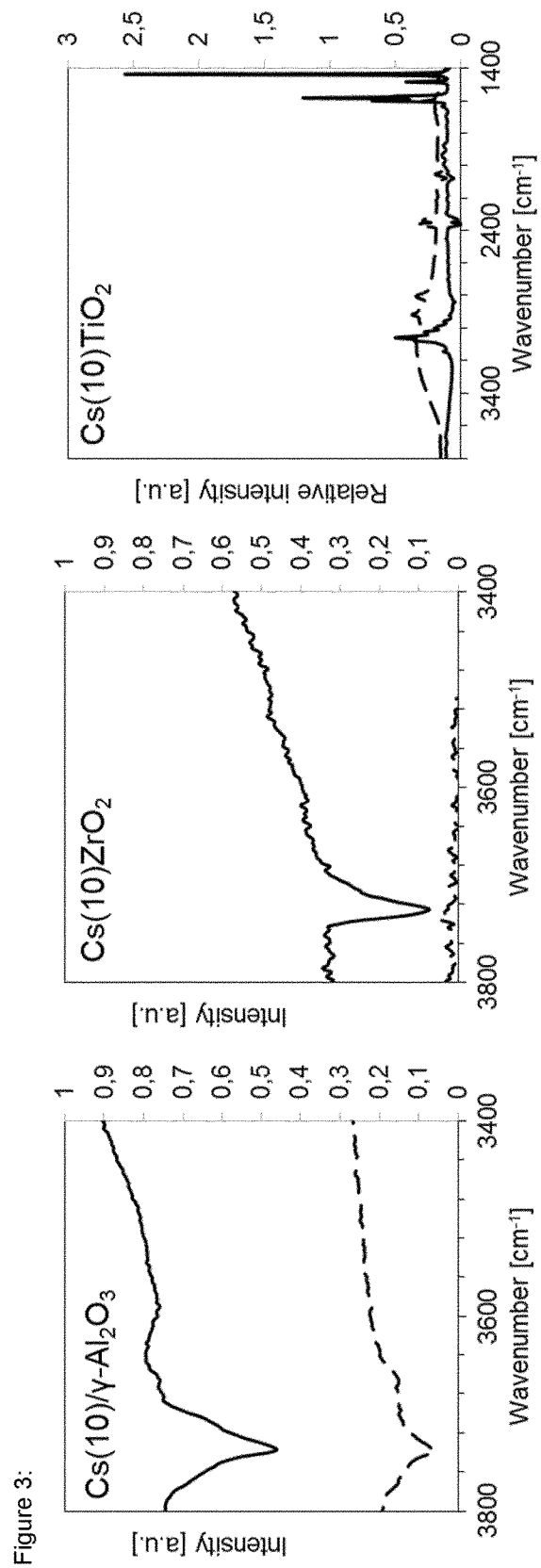
FIG. 3 shows the difference spectra of the OH vibration region of γ-$Al_2O_3$, $ZrO_2$ and $TiO_2$, with the solid line representing the IR spectrum taken a pyridine partial pressure of 0.1 mbar and the broken line representing the IR spectrum taken after evacuation at $10^{-7}$ mbar.

The acidity of the metal oxides was measured with pyridine adsorbed via IR, FIG. 2. On pure γ-$Al_2O_3$ eight bands were observed at 1621, 1612, 1591, 1577, 1450 and 1440 $cm^{-1}$. The bands at 1621 and 1612 $cm^{-1}$ are assigned to the 8a vibrational mode of pyridine coordinatively bound to Lewis acid sites (LAS) of different acid strength (the wavenumber increases with acid strength), while the band at 1579 $cm^{-1}$ is assigned to the 8b vibrational mode. The band at 1591 $cm^{-1}$ is assigned to the 8a vibrational mode of H-bond pyridine, caused by the interaction of pyridine with weak acidic surface hydroxyl groups. The signal at 1450 $cm^{-1}$ are attributed to the 9b vibration of pyridine on LAS, while the band at 1440 $cm^{-1}$ is assigned again to pyridine H-bonded on hydroxyl groups. The sites assigned to pyridine coordinatively bound to LAS (1450 $cm^{-1}$, 1612-1620 $cm^{-1}$) were stable against evacuation, while the H-bonded pyridine bands (1440 and 1593 $cm^{-1}$) disappeared after evacuation due to their weak interaction with the probe molecule. This is in line with the release of OH groups, leading to a decrease in the negative OH band around region of 3700 $cm^{-1}$, as H-bond pyridine desorbed (FIG. 3).

The adsorption of pyridine on $ZrO_2$ and $TiO_2$ via IR gave bands at 1604, 1593, 1573 and 1445 $cm^{-1}$. The 1604 $cm^{-1}$ is assigned to the 8a vibrational mode of pyridine bound to LAS of $ZrO_2$ and $TiO_2$, while the 1573 $cm^{-1}$ is assigned to the 8a vibrational mode. The 1593 $cm^{-1}$ is assigned to the 8a vibrational mode of H-bond pyridine, caused by the interaction of pyridine with weak acidic surface hydroxyl groups. As in the case for γ-alumina, this signal vanished after evacuation. The signal at 1445 $cm^{-1}$ is assigned to the 9b vibration of pyridine on LAS. Integrating the band at 1450 $cm^{-1}$, LAS concentration on the metal oxide was determined as 454 μmol $g^{-1}$ on γ-$Al_2O_3$, 220 μmol $g^{-1}$ on $ZrO_2$ and 749 μmol $g^{-1}$ on $TiO_2$. The shift of the signals of pyridine to lower wavenumbers from γ-$Al_2O_3$ (1450 $cm^{-1}$), to $ZrO_2$ and $TiO_2$ (1445 $cm^{-1}$) shows a higher Lewis acid strength of the former than the latter.

TABLE 3

Summary of all discussed signals of the metal and their assignments.

| Metal oxide | Wavenumber [$nm^{-1}$] | Vibration | Surface species |
|---|---|---|---|
| γ-$Al_2O_3$ | 1620 | $8a_{LAS,strong}$ | $Al^{IV}$ |
| | 1612 | $8a_{LAS,weak}$ | $Al^{IV}$-$Al^{VI}$ |
| | 1593 | $8a_H$ | x-OH |
| | 1573 | 8b | All Al + x-OH |
| | 1450 | $9b_{LAS}$ | All Al |
| | 1440 | $9b_H$ | x-OH |
| $ZrO_2$ | 1604 | $8a_{LAS,weak}$ | $Zr^{IV}$ |
| | 1593 | $8a_H$ | x-OH |
| | 1573 | 8b | $Zr^{IV}$ and x-OH |
| | 1445 | 9b | $Zr^{IV}$ |
| $TiO_2$ | 1604 | $8a_{LAS,weak}$ | $Ti^{IV}$ |
| | 1591 | $8a_H$ | x-OH |
| | 1573 | 8b | $Ti^{IV}$ and x-OH |
| | 1445 | 9b | $Ti^{IV}$ |

Figure 4:
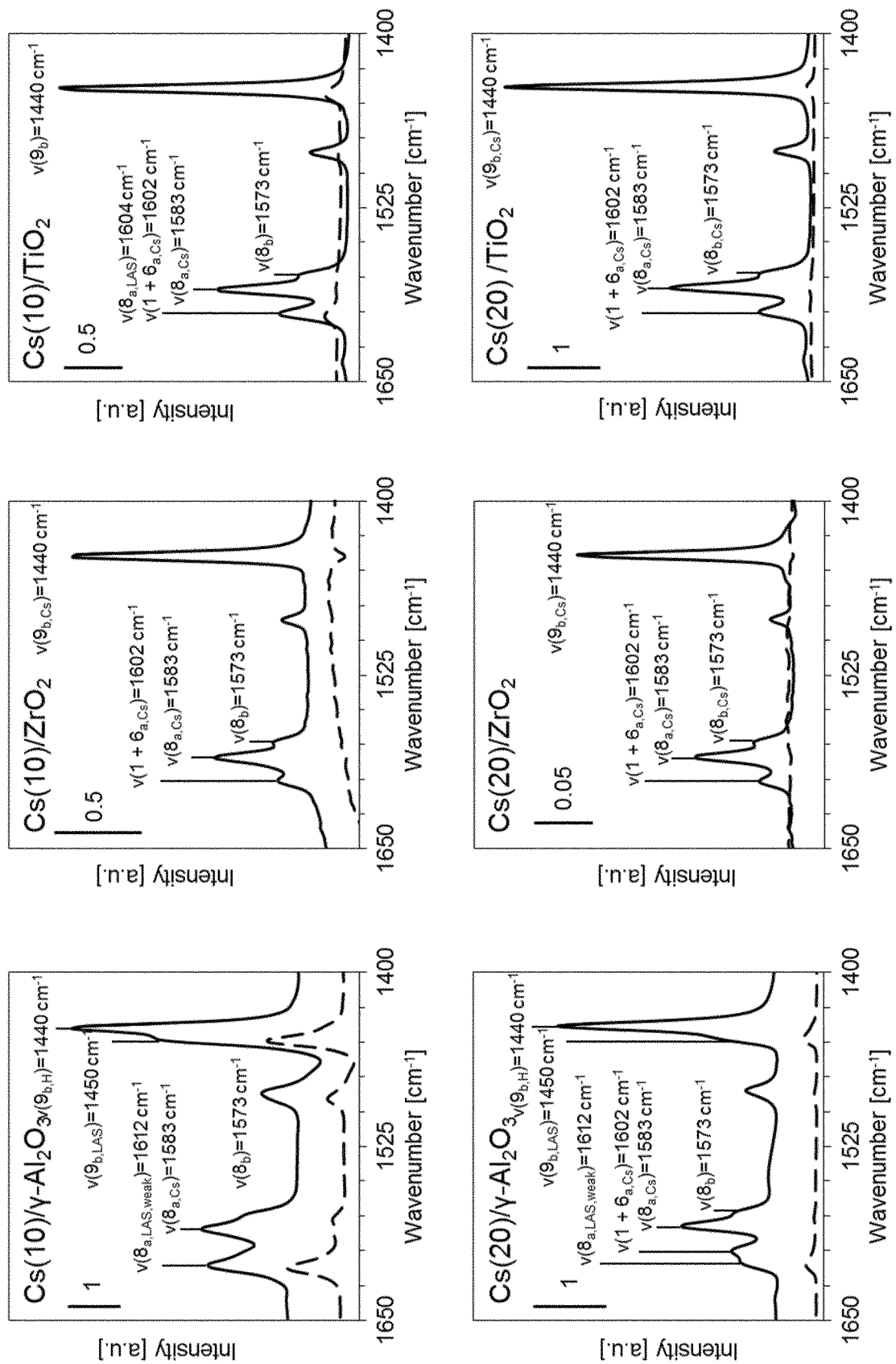
FIG. 4 shows the subtracted IR spectra of metal oxides with Cs loading of 10 or 20 wt.-% at 50° C. with the solid line representing the IR spectrum taken a pyridine partial pressure of 0.1 mbar and the broken line representing the IR spectrum taken after evacuation at $10^{-7}$ mbar.

The addition of Cs on the metal oxides modified the IR spectra with adsorbed pyridine (FIG. 4). On medium doped γ-$Al_2O_3$, Cs(10)γ-$Al_2O_3$, the bands assigned to the 8a vibrational mode of pyridine coordinatively bound to strong (1612 $cm^{-1}$) and weak (1609 $cm^{-1}$) LAS were no longer detected, as well as the signal of H-bonded pyridine. A new band appeared at 1583 $cm^{-1}$, corresponding to the 8a vibrational mode of pyridine coordinatively bound to a weak Lewis acidic alkali, i.e. $Cs^+$ with lower Lewis acid strength than those measured on γ-$Al_2O_3$. Upon addition of Cs on $ZrO_2$ and $TiO_2$, Cs(10)/$ZrO_2$ and Cs(10)/$TiO_2$, the bands assigned to the LAS of the support were not observed. As in the case of Cs/γ-$Al_2O_3$, new bands at 1600 and 1583 $cm^{-1}$ appeared, corresponding to the vibrational mode of the 1+6a and 8a overtone vibrations of pyridine on Cs, respectively. After evacuation, signals of pyridine on Cs sites disappeared on all three samples, remaining partially on Cs(10)/γ-$Al_2O_3$ and Cs(10)/$TiO_2$.

Additional Cs, Cs(20)/γ-$Al_2O_3$, led to a decrease in the band at 1612 $cm^{-1}$. A new signal at 1600 $cm^{-1}$ was observed, attributed to the 1+6a overtone vibration of pyridine on Cs. The already mentioned 1583 $cm^{-1}$ 8a vibration of pyridine on Cs sites and 1573 $cm^{-1}$ 8b vibration of pyridine on LAS and Cs. Thus, the gradual addition of Cs on the surface of γ-$Al_2O_3$ led to the replacement of strong LAS from γ-$Al_2O_3$ with weaker LAS from Cs. Pyridine adsorption on Cs(20)/$ZrO_2$ and Cs(20)/$TiO_2$ catalysts resulted only on pyridine coordinatively bound to $Cs^+$ sites (8a, 8b and 1+6a). All adsorbed pyridine species on Cs doped $ZrO_2$ and $TiO_2$ desorbed under vacuum; while a minor signal of LAS on Cs(20)/γ-$Al_2O_3$ remained.

TABLE 4

Assignments of pyridine absorptions on Cs loaded metal oxides.

| Catalysts | Wavenumber [cm$^{-1}$] | Vibration | Surface species |
|---|---|---|---|
| Cs(10 wt.-%)/ | 1612 | $8a_{LAS,strong}$ | $Al^{IV}$-$Al^{VI}$ |
| γ-$Al_2O_3$ | 1583 | $8a_{Cs}$ | $Cs^+$ |
|  | 1573 | 8b | $Al^{IV}$-$Al^{VI}$ + $Cs^+$ |
|  | 1450 | $9b_{LAS}$ | $Al^{IV}$-$Al^{VI}$ |
|  | 1440 | $9b_{Cs}$ | $Cs^+$ |
| Cs(20 wt.-%)/ | 1612 | $8a_{LAS,strong}$ | $Al^{IV}$-$Al^{VI}$ |
| γ-$Al_2O_3$ | 1602 | $1 + 6a_{Cs}$ | $Cs^+$ |
|  | 1583 | $8a_{Cs}$ | $Cs^+$ |
|  | 1573 | 8b | $Al^{IV}$-$Al^{VI}$ + $Cs^+$ |
|  | 1450 | $9b_{LAS}$ | $Al^{IV}$-$Al^{VI}$ |
|  | 1440 | $9b_{Cs}$ | $Cs^+$ |
| Cs(10 wt.-%)/$ZrO_2$ | 1602 | $1 + 6a_{Cs}$ | $Cs^+$ |
|  | 1583 | $8a_{Cs}$ | $Cs^+$ |
|  | 1573 | $8b_{Cs}$ | $Cs^+$ |
|  | 1440 | $9b_{Cs}$ | $Cs^+$ |
| Cs(20 wt.-%)/$ZrO_2$ | 1602 | $1 + 6a_{Cs}$ | $Cs^+$ |
|  | 1583 | $8a_{Cs}$ | $Cs^+$ |
|  | 1573 | $8b_{Cs}$ | $Cs^+$ |
|  | 1440 | $9b_{Cs}$ | $Cs^+$ |
| Cs(10 wt.-%)/$TiO_2$ | 1604 | $1 + 6a_{Cs}$ | $Cs^+$ |
|  | 1583 | $8a_{Cs}$ | $Cs^+$ |
|  | 1573 | $8b_{Cs}$ | $Cs^+$ |
|  | 1440 | $9b_{Cs}$ | $Cs^+$ |
| Cs(20 wt.-%)/$TiO_2$ | 1602 | $1 + 6a_{Cs}$ | $Cs^+$ |
|  | 1583 | $8a_{Cs}$ | $Cs^+$ |
|  | 1573 | $8b_{Cs}$ | $Cs^+$ |

The titration of the acid sites with pyridine indicates a high heterogeneity of LAS sites in γ-$Al_2O_3$, with two types of LAS, while $TiO_2$ and $ZrO_2$ only provide one type of LAS with similar strength on both materials, being coincident with those observed in literature. The effect of Cs deposition can be rationalized as following: At medium Cs loading, $Cs^+$ modifies the surface sites of the metal oxide by direct interaction, increasing the surface basicity, due to the lower Sanderson electronegativity. This direct interaction is done by exchange of surface protons with $Cs^+$ cations.

At high Cs loading, the surface is dominated by Cs. As postulated for potassium on $TiO_2$, high loading of alkali leads to a complete coverage of the metal oxide surface, leading to surface properties similar to the bulk alkaline material.

2.5 CO Absorption

Figure 5:
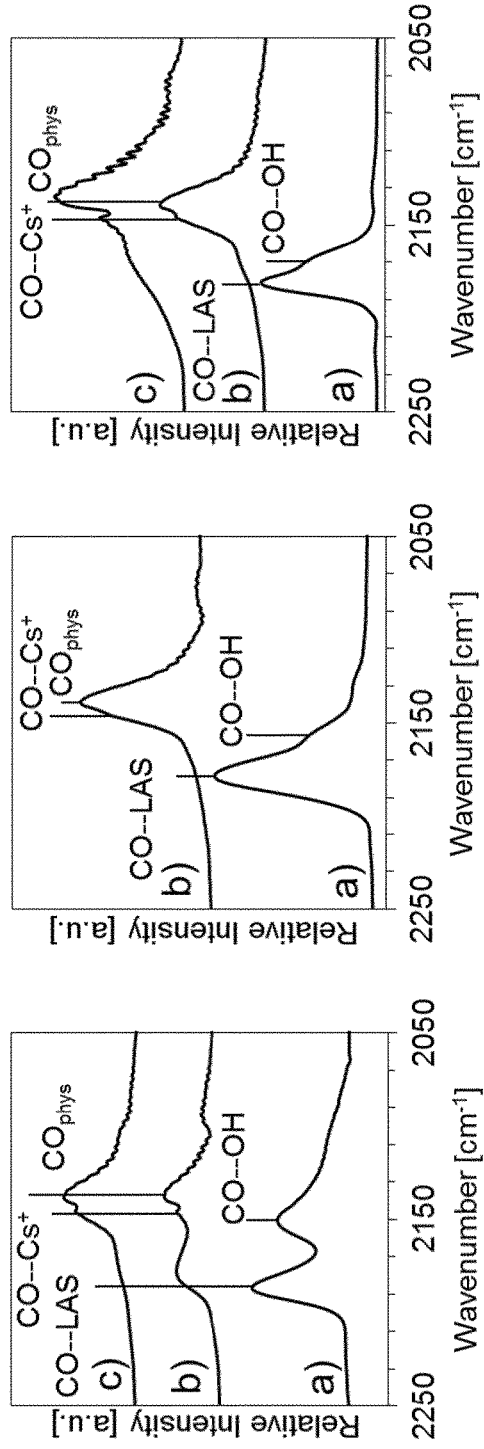
FIG. 5 shows the IR spectra of CO adsorption on γ-$Al_2O_3$ (left), $ZrO_2$ (middle), and $TiO_2$ (right) at a CO partial pressure of 5 mbar and −150° C., with (a) the pure metal oxides, (b) Cs loading of 10 wt.-%, and (c) Cs loading of 20 wt.-%.

The CO adsorption on the catalysts via IR is shown in FIG. 5. The assignments for the different CO bands are in Table 4. Similar IR bands were obtained in the adsorption of CO on the different metal oxides. The bands in between 2180-2190 cm$^{-1}$ are assigned to CO adsorption on LAS, while those around 2150 cm$^{-1}$ are assigned to surface hydroxyl. The CO stretching vibration in γ-$Al_2O_3$ (2188 cm$^{-1}$) was at higher wavenumber than $ZrO_2$ (2177 cm$^{-1}$) and $TiO_2$ (2181 cm$^{-1}$), indicative of a higher perturbation of the CO bond. This trend is the same as the one observed with pyridine, implying a higher strength of the Lewis acid sites of γ-$Al_2O_3$.

The addition of 10 wt % Cs on the three supports led to a decrease of the CO stretching vibration on LAS to lower wavenumbers (2138-2136 cm$^{-1}$), corresponding to CO adsorbed on $Cs^+$ ions. In the case of Cs(10)/γ-$Al_2O_3$, an additional band appeared at 2179 cm$^{-1}$, corresponding to LAS in the γ-$Al_2O_3$ support altered by the alkali cation. No bands were observed for CO adsorbed on OH groups. On the samples with high Cs loading of 20 wt % only the signals of CO on Cs cations and physisorbed CO were detected. CO did not adsorb on the Cs(20)/$ZrO_2$ sample.

The red shift of the CO stretching vibration on LAS with Cs on the surface of γ-$Al_2O_3$ is due to an increase in the basicity, decreasing the Sanderson electronegativity. The results for $TiO_2$ and $ZrO_2$ are in line with the results of pyridine adsorption, with no LAS being accessible on those materials at 10 wt % Cs loading. As in the case of the pyridine adsorption, $Cs^+$ is the only species available for CO adsorption on the heavy Cs doped materials. The adsorption of CO via IR is in line with the pyridine adsorption; Lewis acid sites from the support are not present with 10 wt % Cs loading, with the exception of Cs(10)/γ-$Al_2O_3$.

TABLE 5

Assignments of CO absorptions on pure and Cs loaded metal oxides.

| | Metal oxides | | | | Cs (10 wt.-%) | | | | Cs (20 wt.-%) | | | |
|---|---|---|---|---|---|---|---|---|---|---|---|---|
| | $CO_{LAS}$ | $CO_{OH}$ | $CO_{Cs+}$ | $CO_{Phys}$ | $CO_{LAS}$ | $CO_{OH}$ | $CO_{Cs+}$ | $CO_{Phys}$ | $CO_{LAS}$ | $CO_{OH}$ | $CO_{Cs+}$ | $CO_{Phys}$ |
| γ-$Al_2O_3$ | 2188 | 2150 | — | — | 2179 | — | 2146 | 2136 | — | — | 2146 | 2136 |
| $ZrO_2$ | 2177 | 2154 | — | — | — | — | 2144 | 2136 | — | — | — | — |
| $TiO_2$ | 2181 | 2150 | — | — | — | — | 2144 | 2138 | — | — | 2144 | 2133 |

2.6 Methanol Absorption

Figure 6:
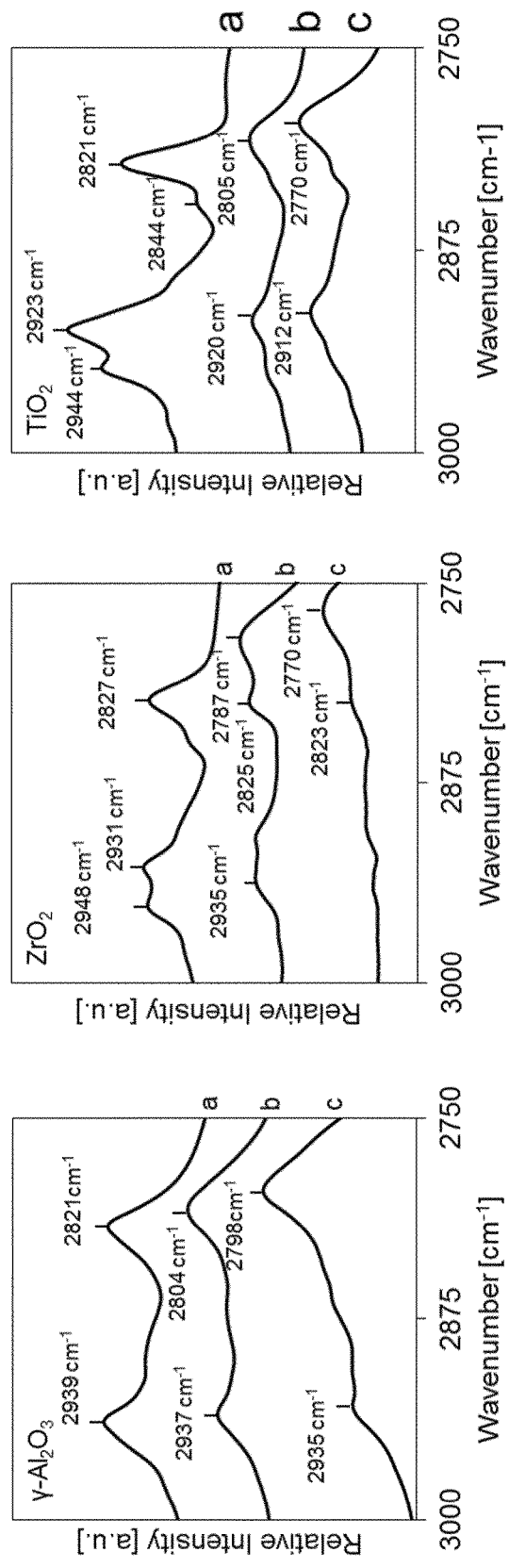
FIG. 6 shows the IR spectra of methanol adsorbed on $Al_2O_3$ (left), $ZrO_2$ (middle) and $TiO_2$ (left) at a methanol partial pressure of 0.1 mbar and 50° C., with (a) the pure metal oxides, (b) Cs loading of 10 wt.-%, and (c) Cs loading of 20 wt.-%.
Figure 7:
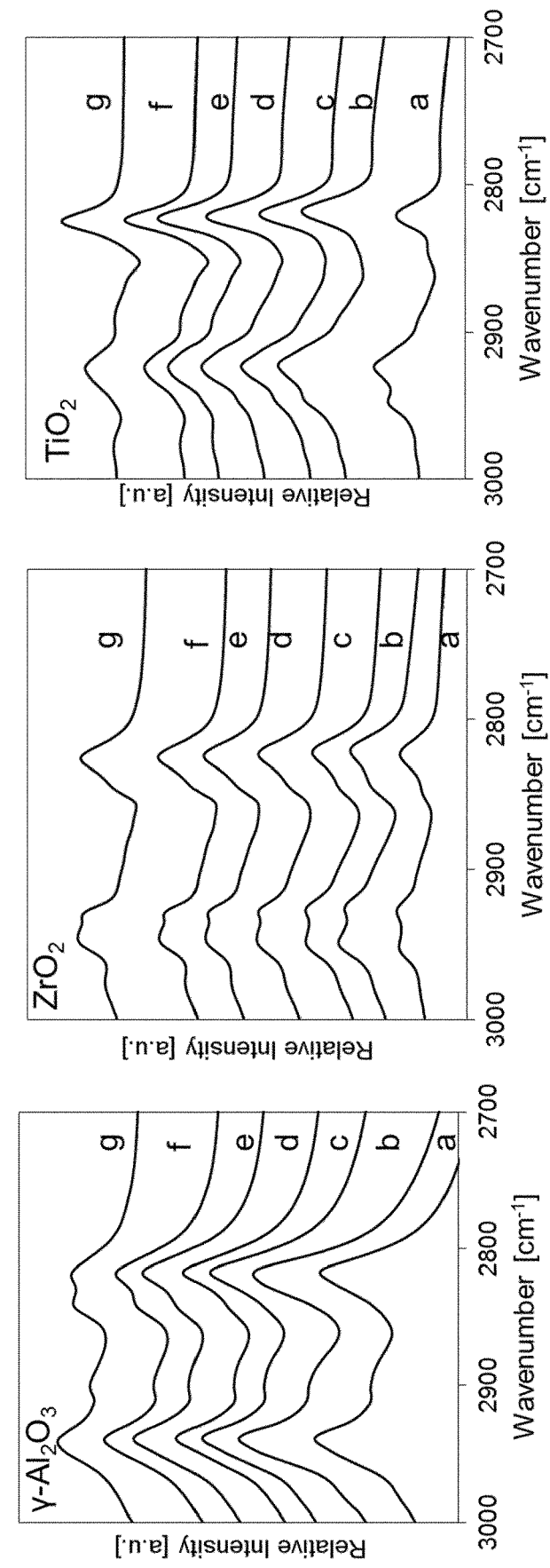
FIG. 7 shows the IR spectra of methanol adsorption on the pure metal oxides γ-$Al_2O_3$ (left), $ZrO_2$ (middle) and $TiO_2$ (right) at methanol partial pressures and temperature of (a) 50° C. and 0.1 mbar, (b) 50° C. and 1 mbar, (c) 100° C. and 1 mbar, (d) 150° C. and 1 mbar, (e) 200° C. and 1 bar, (f 250° C. and 1 mbar, and (g) 300° C. and 1 mbar.
Figure 8:
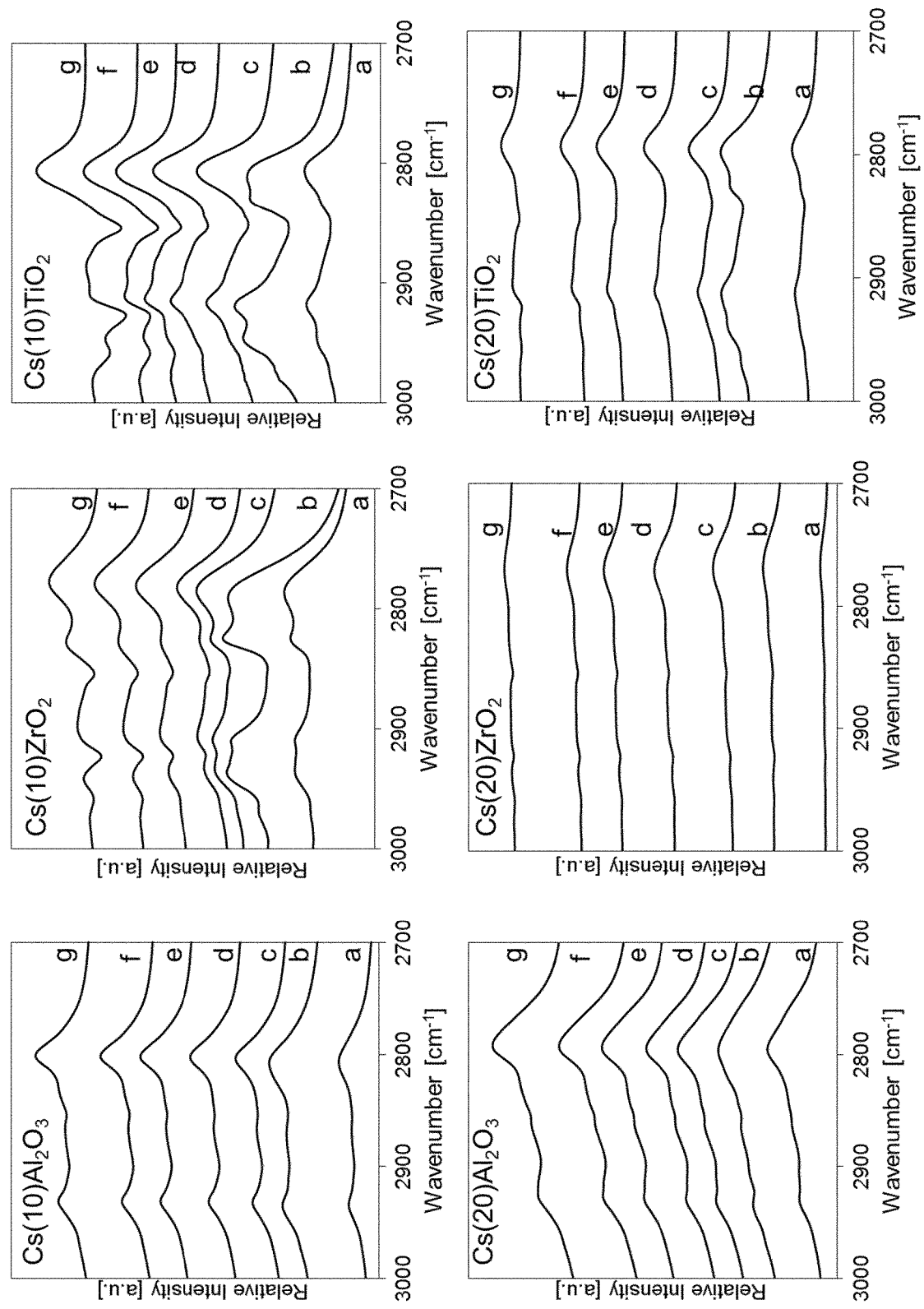
FIG. 8 shows the IR spectra of methanol over γ-$Al_2O_3$ with 10 and 20 wt.-% Cs (left), $ZrO_2$ with 10 and 20 wt.-% Cs (middle), and $TiO_2$ with 10 and 20 wt.-% Cs (right) at methanol partial pressure and temperatures of (a) 50° C. and 0.1 mbar, (b) 50° C. and 1 mbar, (c) 100° C. and 1 mbar, (d) 150° C. and 1 mbar, (e) 200° C. and 1 mbar, (f 250° C. and 1 mbar, and (g) 300° C. and 1 mbar.

The IR spectra of methanol adsorbed on the metal oxides and its Cs doped are shown in FIG. 6, exhibiting bands in the 3000-2750 cm$^{-1}$ region (alkyl (sp$^3$) C—H vibrations). The region in between 3000-2900 cm$^{-1}$ is assigned to the asymmetric stretch of ($\upsilon_{as}$(CH$_3$)) or its Fermi resonance with CH$_3$ deformation vibrations (2$\delta_s$(CH$_3$)), while lower bands are assigned to symmetric stretching vibrations ($\upsilon_s$(CH$_3$)). Different intensities were observed for the IR bands assigned to the adsorption of methanol on strong Lewis acid sites and strong Lewis basic sites, for both the $\upsilon_{as}$ and the $\upsilon_s$ at 50° C. (FIGS. 6 to 8). The former site led to the formation of a bridging methoxide, known as Species I, with IR bands at higher wavenumber for both the $\upsilon_{as}$ (2943, 2948 and 2944 cm$^{-1}$ for γ-$Al_2O_3$, $ZrO_2$ and $TiO_2$) and the $\upsilon_s$ (2845, 2852 and 2844 cm$^{-1}$ for γ-$Al_2O_3$, $ZrO_2$ and $TiO_2$). The latter site resulted in the formation of an alcoholate (dissociation of the O—H group), known as Species II, for both the $\upsilon_{as}$ (2939, 2931 and 2923 cm$^{-1}$ for γ-Al$_2$O$_3$, ZrO$_2$ and TiO$_2$) and the $\upsilon_s$ (2821, 2827 and 2821 cm$^{-1}$ for γ-Al$_2$O$_3$, ZrO$_2$ and TiO$_2$). On ZrO$_2$ a relatively higher concentration of dissociated methanol was visible, which increased further for TiO$_2$. In the case of γ-Al$_2$O$_3$, heating of IR cell led to an increase in the intensity of the bridging methoxides (Species I). No major changes were observed upon heating in the other two supports. The relative intensities of methanol on the surface species directly leads to the conclusion that the general acidic character of the metal oxide to a more basic one decreases in the order γ-Al$_2$O$_3$>ZrO$_2$~TiO$_2$.

3. Catalytic Testing of the Supported Catalysts According to the Invention

The catalytic thiolation of methanol was performed in a reaction tube with a volume of 25 mL. Before the reaction, 125.0 mg of catalyst (125-250 μm), diluted in 1 g of SiC, were sulfided in a flow of 20 mL min$^{-1}$ H$_2$S at 360° C. and 9 bar. The volume of the catalyst was almost negligible compared to the empty volume of the plug flow reactor (20 mL). This led to a relatively low Liquid Hourly Space Velocity (LHSV) based on liquid methanol (CH$_3$OH) of only 0.054 h$^{-1}$. The Gas Hourly Space Velocity (GHSV) based on the complete feed (H$_2$S, CH$_3$OH and N$_2$) was 150 h$^{-1}$ (based on standard conditions at 0° C. and 1.013 bar in accordance with DIN 1343). To determine activation energies, the reaction was performed with a flow of gaseous CH$_3$OH (10 mL min$^{-1}$) mixed with H$_2$S (20 mL min$^{-1}$) and N$_2$ (20 mL min$^{-1}$) at a pressure of the feed stream of 9 bar with partial pressures of 3.6 bar for N$_2$, 3.6 bar for H$_2$S and 1.8 bar for methanol. The reaction tube was heated via a jacket by means of a heat transfer medium to temperatures between 300 and 360° C.

Standard calculations of the Weisz-Prater modulus showed that it was <1 for all catalysts under all conditions, and, therefore, it can be concluded that the kinetic results were unaffected by internal mass transfer effects. Online analysis of the product flow was done using a Shimadzu GC-2014 equipped with a HP plot Q column (2.7 m, 2.0 mm inner diameter), using a TCD detector. Reaction rate constants were calculated using the integrated rate law for a 0.5 order reaction in CH$_3$OH and H$_2$S for CH$_3$SH. To study the product distribution over the whole range of conversion, the residence time was adjusted, keeping partial pressure of CH$_3$OH at 2.2 bar, and N$_2$ and H$_2$S at 3.3 bar at 360° C.

Reaction orders were determined at 360° C. For reaction orders in H$_2$S, the partial pressure of methanol was kept constant at 2.2 bar, while the H$_2$S partial pressure was varied between 1.1 and 5.6 bar. To measure methanol reaction orders, the H$_2$S partial pressure was set to 4.5 bar and the CH$_3$OH partial pressure varied from 0.6 mbar to 2.2 gaseous CH$_3$OH. The N$_2$ gas flow was adjusted to compensate volume flow changes and keep the total volume flow constant at 80 ml/min. The amount of catalyst used in each experiment was adjusted accordingly, to ensure CH$_3$OH conversion below 10%. Reaction orders for cesium-modified materials were measured with 10.0 mg catalysts, while 5.0 mg for TiO$_2$ and ZrO$_2$ and 1.0 mg of γ-Al$_2$O$_3$ was sufficient. In the case of γ-Al$_2$O$_3$, the catalyst was physically mixed with SiO$_2$, being known to be inactive in the studied reaction, in a ratio of 1:9, to avoid channeling effects.

3.1 Catalytic Activity

Figure 9:
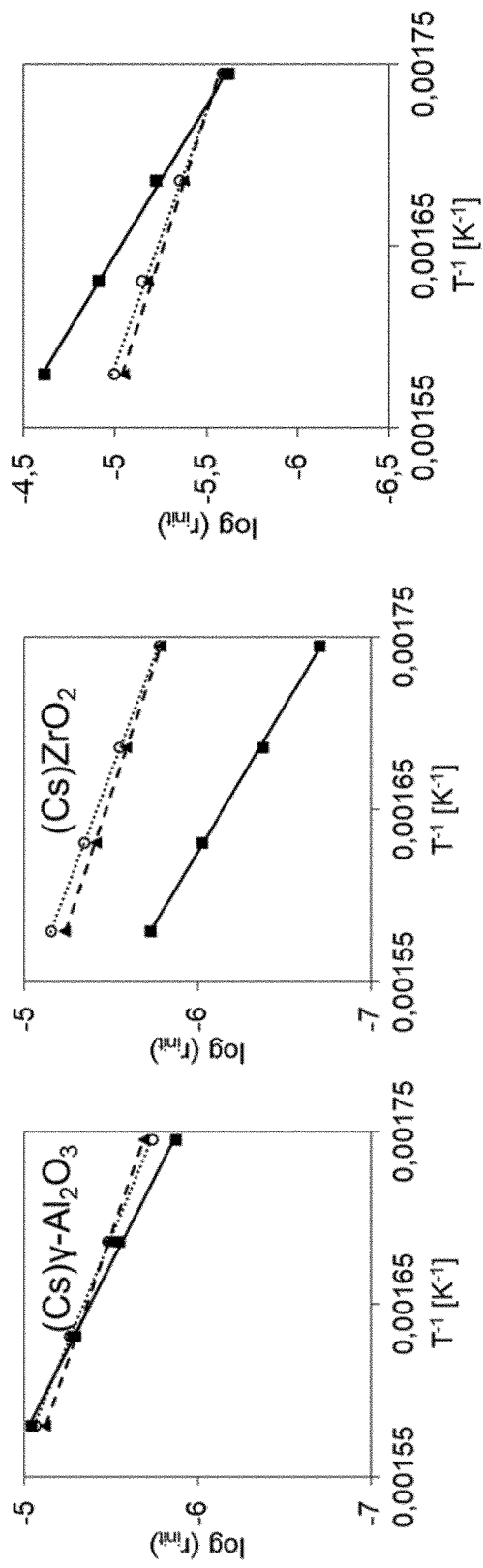
FIG. 9 shows the initial rates for methyl mercaptan formation over γ-$Al_2O_3$ (left), $ZrO_2$ (middle) and $TiO_2$ (right) between 300 and 360° C. for pure metal oxides (solid line with cubes), Cs loading of 10 wt.-% (dotted line with circles), and Cs loading of 20 wt.-% (broken line with triangles)

Initial rates for methyl mercaptan (CH$_3$SH) formation are shown in FIG. 9. The highest rate in methanol thiolation was observed for TiO$_2$ (0.17-1.4·10$^{-6}$ mol$_{CH3SH}$ s$^{-1}$ g$_{cat}^{-1}$), followed by γ-Al$_2$O$_3$ (0.13-9.2·10$^{-6}$ mol$_{CH3SH}$ s$^{-1}$ g$_{cat}^{-1}$) and ZrO$_2$ (0.02-0.2·10$^{-6}$ mol$_{CH3SH}$ s$^{-1}$ g$_{cat}^{-1}$). For the Cs doped systems the rates for CH$_3$SH formation decreased in the order of Cs(10 wt.-%)/γ-Al$_2$O$_3$ (1.8-8.7·10$^{-6}$ mol$_{CH3SH}$ s$^{-1}$ g$_{cat}^{-1}$)>Cs(10 wt.-%)/ZrO$_2$ (1.7-7.1·10$^{-6}$ mol$_{CH3SH}$ s$^{-1}$ g$_{cat}^{-1}$ g$_{cat}^{-1}$)>Cs(10 wt.-%)/TiO$_2$ (1.8-6.6·10$^{-6}$ mol$_{CH3SH}$ s$^{-1}$ g$_{cat}^{-1}$). Higher Cs loading of 20 wt % did not lead to more active catalysts, rather the activity was slightly lower for Cs(20 wt.-%)/γ-Al$_2$O$_3$ (2.0-7.6·10$^{-6}$ mol$_{CH3SH}$ s$^{-1}$ g$_{cat}^{-1}$), Cs(20 wt.-%)/ZrO$_2$ (1.7-7.1·10$^{-6}$ mol$_{CH3SH}$ s$^{-1}$ g$_{cat}^{-1}$) and Cs(20 wt.-%)/TiO$_2$ (1.8-5.8·10$^{-6}$ mol$_{CH3SH}$ s$^{-1}$ g$_{cat}^{-1}$). While there is one magnitude difference in the rates of CH$_3$SH formation with the different metal oxides, the activity of the Cs systems showed only minor differences. This indicates that the overall activity is determined by the surface Cs species, which appears to be similar on all three metal oxide supports. Indeed, the CH$_3$SH formation rate decreased slightly for all three systems.

Figure 10:
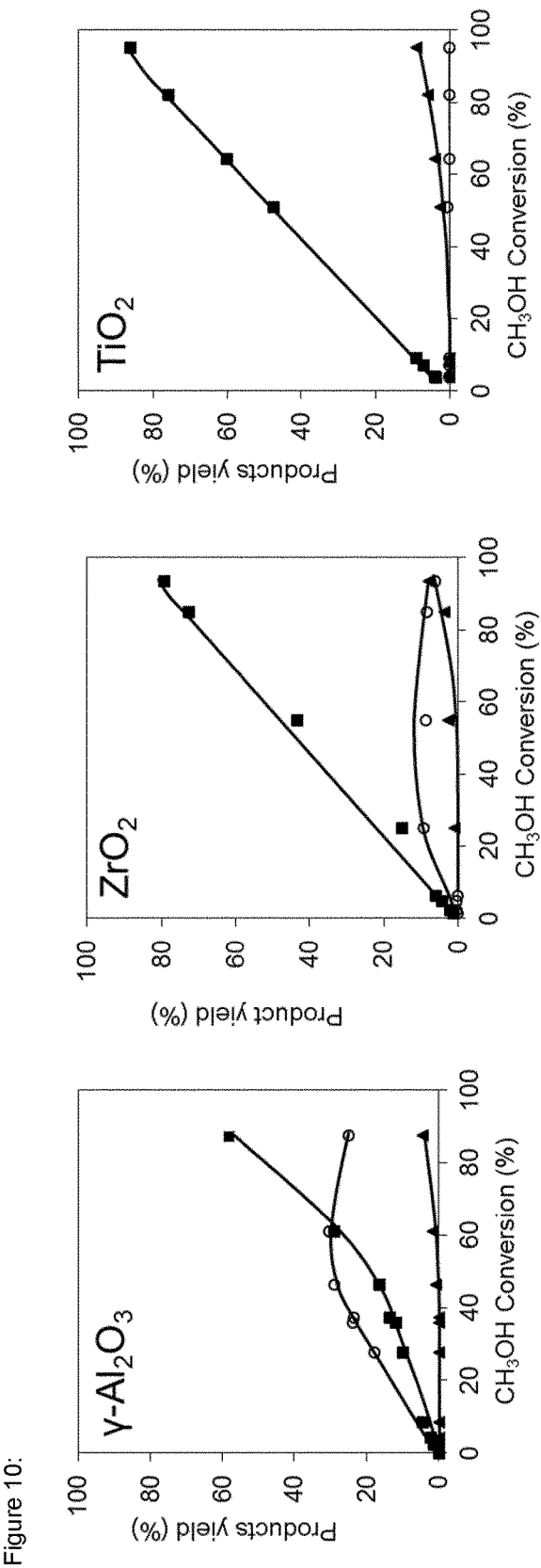
FIG. 10 shows the yields for methyl mercaptan (cubes), dimethyl ether (circles) and dimethyl sulfide (triangles) as a function of methanol conversion over the pure metal oxides γ-$Al_2O_3$ (left), $ZrO_2$ (middle) and $TiO_2$ (right) at 360° C.
Figure 11:
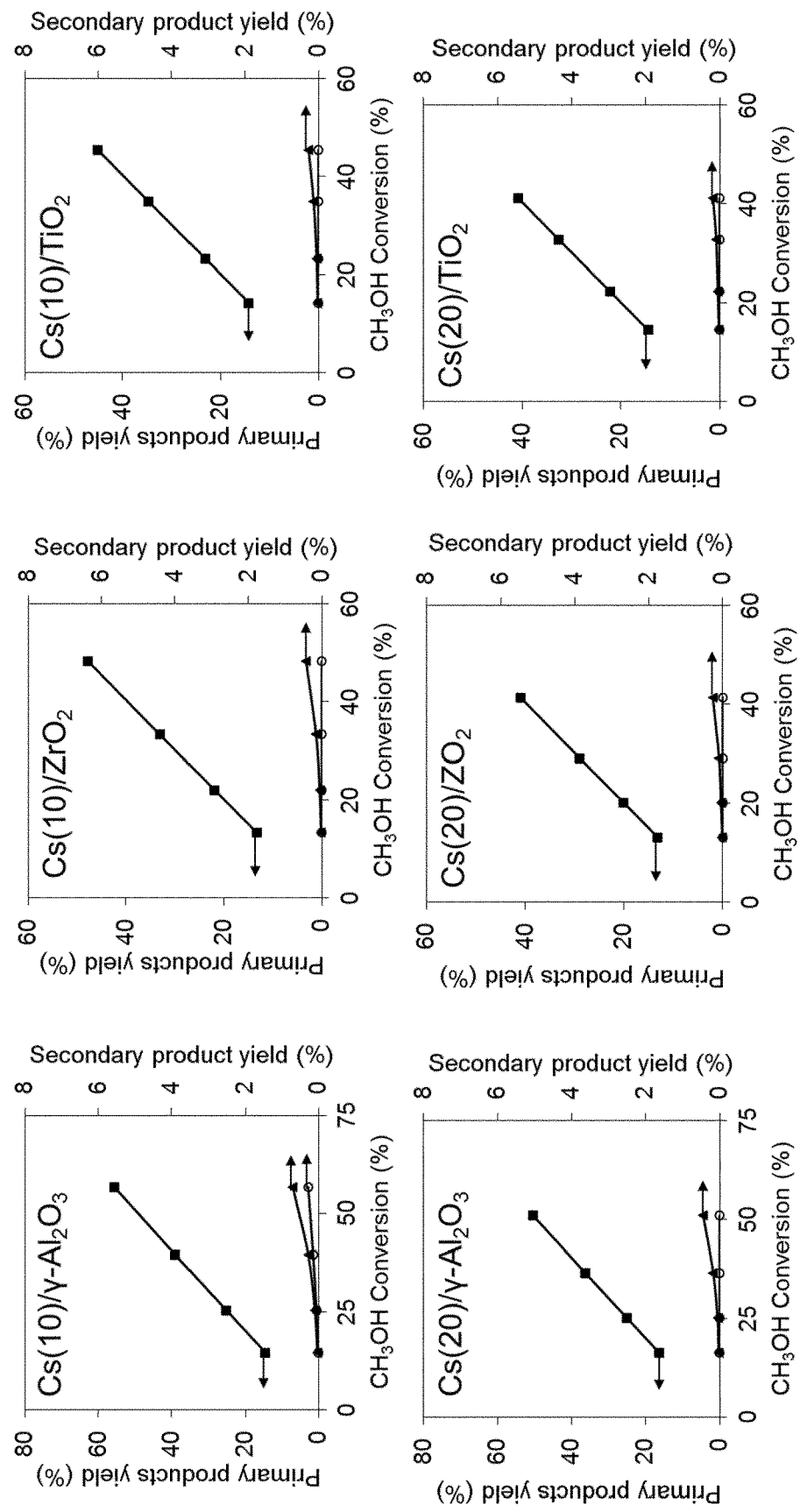
FIG. 11 shows the yields for methyl mercaptan (cubes), dimethyl ether (circles) and dimethyl sulfide (triangles) as a function of methanol conversion over γ-$Al_2O_3$ with 10 and 20 wt.-% Cs (left), $ZrO_2$ with 10 and 20 wt.-% Cs (middle), and $TiO_2$ with 10 and 20 wt.-% Cs (right) at temperatures between 300 and 360° C.

The yields of methyl mercaptan, dimethyl sulfide (DMS), and dimethyl ether (DME) were measured as a function of the methanol conversion at 360° C. for all three metal oxides (FIG. 10). On γ-Al$_2$O$_3$, CH$_3$SH and (DME) were obtained as primary products, being DME the highest primary product until 60% of methanol conversion. Overcoming 60% conversion the yield of DME decreases to 20% at 90% conversion, being CH$_3$SH the main product. This behavior is explained by the re-adsorption of DME on the catalyst, undergoing secondary reaction to form CH$_3$SH. Similar results were observed with ZrO$_2$, being CH$_3$SH the main primary product and a dimethyl ether yield below 10%. Remarkably, no DME was formed at conversion lower 10% on ZrO$_2$. On both γ-Al$_2$O$_3$ and ZrO$_2$ dimethyl sulfide was found at higher conversion levels, being a secondary product of CH$_3$SH formation. On TiO$_2$ no dimethyl ether was observed, being dimethyl sulfide the only byproduct. Performing the reaction without H$_2$S on ZrO$_2$ and TiO$_2$ resulted in the formation of DME (FIG. 10), hinting for a competition between the reactants on ZrO$_2$ and TiO$_2$. The yields to CH$_3$SH increases in the order γ-Al$_2$O$_3$<ZrO$_2$<TiO$_2$. The yields of CH$_3$SH, DMS, and DME were measured as a function of the CH$_3$OH conversion at 360° C. for all three metal oxides with loading of 10 and 20 wt.-% of Cs (FIG. 11). A general trend was observed for all Cs containing systems: CH$_3$SH was obtained as main product, while the only catalyst yielding DME was Cs(10 wt.-%)/Al$_2$O$_3$, with a DME yield of 0.3% at 360° C. Main side product was DMS, with a maximum yield of 0.7% on Cs(10 wt.-%)/Al$_2$O$_3$ at 360° C. The absence of DME with Cs present on the surface was attributed to the absence of strong LAS. These results are supported with the adsorption of pyridine and CO via IR, showing a drastic decrease of Lewis acidity by Cs doping.

3.2 Kinetics
a) Formation of Methyl Mercaptan

Figure 12:
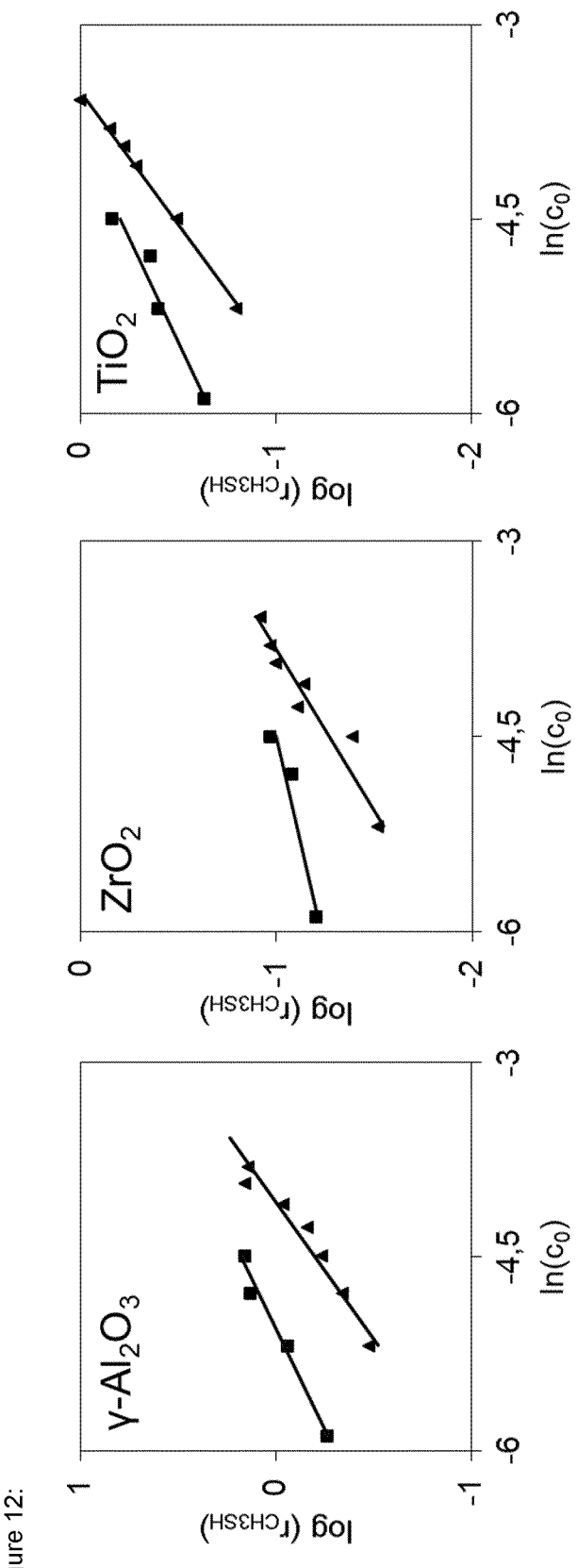
FIG. 12 shows the dependency of methyl mercaptan formation rates over γ-$Al_2O_3$ in methanol (cubes; y=0.3x+1.7) and hydrogen sulfide (triangles; y=0.5x+1.9), $ZrO_2$ in methanol (cubes; y=0.2x−0.3) and hydrogen sulfide (triangles; y=0.4x−0.6) and $TiO_2$ in methanol (cubes; y=0.3x+1.2) and hydrogen sulfide (triangles; y=0.5x+1.7) with the concentration in mol/l.
Figure 13:
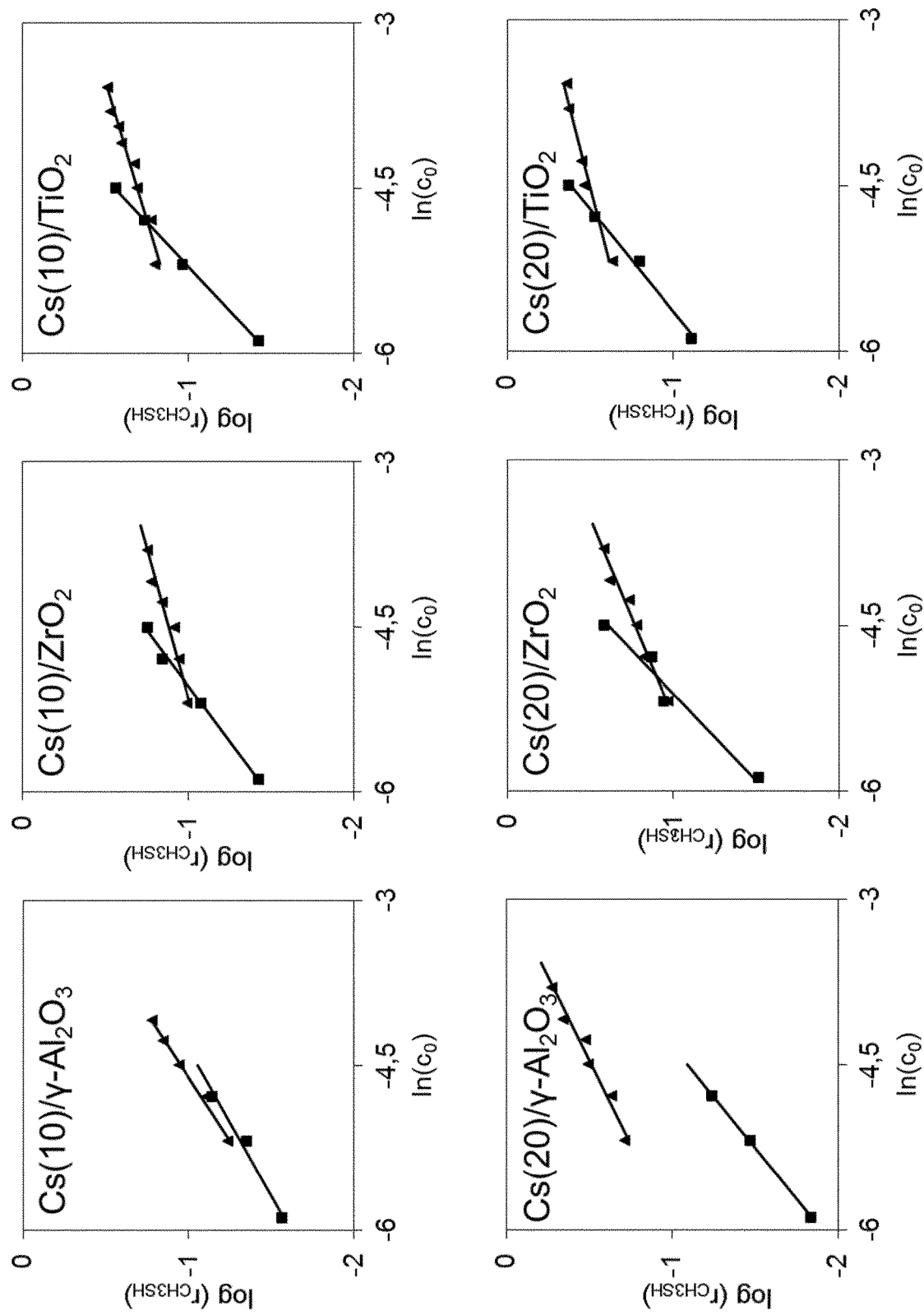
FIG. 13 shows the dependency of methyl mercaptan formation rates over catalysts with different loadings of cesium: 10 wt.-% Cs (first row) in methanol indicated by cubes (γ-$Al_2O_3$: y=0.4x+1.0; $ZrO_2$: y=0.5x+1.5; and $TiO_2$: y=0.6x+2.3) and in hydrogen sulfide indicated by triangles (γ-$Al_2O_3$: y=0.4x+0.6; $ZrO_2$: y=0.3x−0.01; and $TiO_2$: y=0.2x+0.2). 20 wt.-% Cs (second row) in methanol indicated by cubes (γ-$Al_2O_3$: y=0.3x+1.0; $ZrO_2$: 0.6x+2.3; and $TiO_2$: y=0.5x+2.0) and in hydrogen sulfide indicated by triangles (γ-$Al_2O_3$: y=0.5x+1.3; $ZrO_2$: y=0.3x+0.5; and $TiO_2$: y=0.2x+0.3), concentrations in mol/l.

The dependency of the methyl mercaptan formation rates in methanol and hydrogen sulfide over the pure metal oxides in FIG. 12 and over the metal oxides with a loading of 10 and 20 wt.-% Cs in FIG. 13. The reaction orders for the formation of methyl mercaptan, with respect to CH$_3$OH and H$_2$S are shown in Table 6.

TABLE 6

Determined reaction order for methyl mercaptan
formation in H$_2$S and CH$_3$OH on all tested systems.

| Support material | Kinetics | Catalyst loading | | |
|---|---|---|---|---|
| | | 0 | 10 | 20 |
| Al$_2$O$_3$ | Reaction | 0.4 | 0.5 | 0.3 |
| TiO$_2$ | order | 0.3 | 0.6 | 0.6 |
| ZrO$_2$ | (Methanol) | 0.3 | 0.5 | 0.6 |
| Al$_2$O$_3$ | Reaction | 0.4 | 0.4 | 0.6 |
| TiO$_2$ | order | 0.5 | 0.2 | 0.2 |
| ZrO$_2$ | (H$_2$S) | 0.4 | 0.2 | 0.2 |

On all metal oxides, the reaction order of 0.5 in both H$_2$S and CH$_3$OH in the formation of CH$_3$SH hints for the dissociation of both reactants, prior to the bimolecular Langmuir-Hinshelwood mechanism. The rate equation for methyl mercaptan is $$r_{CH_3SH} = \frac{k_5 K_2 K_3 [CH_3OH]^{0.5}[H_2S]^{0.5}}{a^2} \text{ with}$$

$$a = \left(1 + K_2^{0.5}[CH_3OH]^{0.5} + K_3^{0.5}[H_2S]^{0.5} + [CH_3SH]^{0.5}/K_6^{0.5} + [H_2O]^{0.5}/K_7^{0.5}\right).$$

The rate equation for dimethyl ether is $$r_{CH_3OCH_3} = \frac{k_4 K_1 [CH_3OH]^{1.5}}{b} \text{ with}$$

$$b = \left(1 + K_1^{0.5}[CH_3OH]^{0.5} + [H_2O]^{0.5}/K_8^{0.5}\right).$$

Hydrogen sulfide is known to adsorb dissociatively on the surface of metal oxides, while methanol also adsorbs dissociatively forming a methanolate on the Lewis acid-base pairs of the surface oxides. Thus, it is believed that both substrates dissociate on the same kind of basic sites. One could speculate that a decrease in the reaction order with partial pressure would have the effect that the substrates were competing for adsorption on the surface. However, this is not observed in the case of metal oxides.

The apparent activation energy for methyl mercaptan formation was found to be around 112 kJ mol$^{-1}$ on γ-Al$_2$O$_3$, 115 kJ mol$^{-1}$ on ZrO$_2$ and 107 kJ mol$^{-1}$ on TiO$_2$. This is the apparent activation energy of methyl mercaptan formed over the active sites of the metal oxides, as no Cs is present.

TABLE 7

Determined apparent activation energy for
methyl mercaptan formation.

| | | Cs loading [wt.-%] | | |
|---|---|---|---|---|
| | | 0 | 10 | 20 |
| Al$_2$O$_3$ | E$_{a,app,CH3SH}$ | 112 | 78 | 65 |
| TiO$_2$ | [kJ mol$^{-1}$] | 107 | 66 | 59 |
| ZrO$_2$ | | 115 | 73 | 64 |

The addition of Cs (10 wt.-%) resulted in a reaction order close to 0.5 in both reactants, hinting to the same dissociative reaction mechanism as proposed for the pure metal oxides. However, the reaction order of 0.2 on H$_2$S suggests that the Cs/TiO$_2$ and Cs/ZrO$_2$ catalysts are operating under partial coverage of H$_2$S. The apparent activation energy decreased to values in between 66 to 78 kJ mol$^{-1}$. The lower activation energy of these catalysts, with respect to the metal oxides, is associated to an increase in basicity. The presence of the Cs$^+$ cation on the support hints for the coverage of its surface hydroxyls, similarly to that observed with sodium and potassium on alumina. This was confirmed with the absence of the OH bands during adsorption of pyridine and CO via IR. On all heavy Cs doped materials (20 wt.-%), similar reaction order values were obtained as for Cs 10 wt.-%, also hinting for a dissociative mechanism. The apparent activation barrier was in between 65-59 kJ mol$^{-1}$ for the three heavy doped materials. The decrease of apparent activation energy can be explained by a complete modification of the surface. As shown by pyridine adsorption, the only surface species available during pyridine adsorption was Cs, suppressing the chemical properties of the metal oxides and acting as a very weak LAS. In addition, the absence of strong Lewis acid sites resulted only in the formation of surface methanolate, as observed during methanol adsorption via IR on the heavy Cs doped catalysts.

Figure 14:
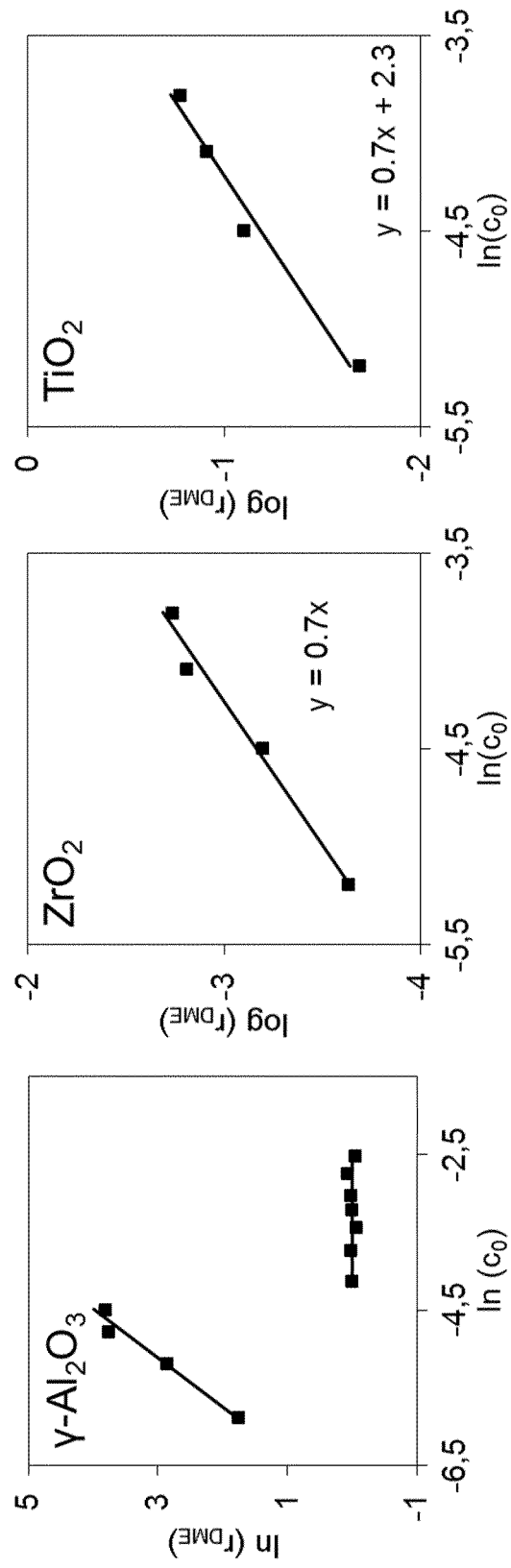
FIG. 14 shows the dependency of dimethyl ether formation rate over pure γ-$Al_2O_3$ in methanol (indicated by cubes; y=1.5x+11.0) and in hydrogen sulfide (indicated by triangles y=0.0x), over pure $ZrO_2$ in methanol (indicated by cubes; y=0.7x) and over pure $TiO_2$ (indicated by cubes; y=0.7x+2.3), concentration in mol/l.

The reaction orders for DME formation were determined for all pure metal oxides in methanol and hydrogen sulfide (table 8 and FIG. 14). The reaction order for dimethyl ether formation was 1.5 in methanol and 0 in H$_2$S on γ-Al$_2$O. Zero order in H$_2$S shows that H$_2$S does not compete with methanol on DME formation sites. The reaction order of 1.5 in methanol is explained by the partially coverage of the catalyst surface by methanol. On γ-Al$_2$O$_3$, the adsorption of methanol seems to be favored compared to H$_2$S, leading to DME formation and zero order in H$_2$S. On ZrO$_2$ and TiO$_2$ reaction order for DME formation (without H$_2$S present) was found to be 0.7. It is believed that on these materials surface coverage of methanol is higher compared to γ-Al$_2$O. The lower apparent activation energy on γ-Al$_2$O$_3$ compared to the other two materials is attributed to the higher Lewis acid strength, as shown by CO and pyridine adsorption, facilitating the break of the CO bond of CH$_3$OH.

TABLE 8

Reaction in methanol and hydrogen sulfide and
apparent activation energy for dimethyl ether
formation.

| Support | Reaction order (Methanol) | Reaction order (H$_2$S) | E$_{a,app,DME}$ [kJ mol$^{-1}$] |
|---|---|---|---|
| Al$_2$O$_3$ | 1.5 | 0 | 70 |
| TiO$_2$ | 0.7 | n.d. | 91 |
| ZrO$_2$ | 0.7 | n.d. | 93 |

3.3 Catalytic Selectivity

For the pure metal oxide catalysts, γ-Al$_2$O$_3$ had the lowest selectivity for the formation of methyl mercaptan, with dimethyl ether being the main product in the temperature range between 300 and 320° C. (with S$_{DME, 300° C.}$=71.2% and S$_{DME, 320° C.}$=63.4%). With increasing temperature, the selectivity to dimethyl ether decreased to S$_{DME, 340° C.}$=49.8% and finally S$_{DME, 360° C.}$=28.6%). As dimethyl ether selectivity decreased, the methyl mercaptan selectivity increased from 28.5% at 300° C. to 71.2% at 360° C. The selectivity for the formation of dimethyl sulfide was less than 5%.

On pure ZrO$_2$, the selectivity for the formation of methyl mercaptan was 53.1% at 300° C. and 60% at 360° C. Again, the major side product was dimethyl ether, however, with a selectivity decreasing from 46.7% at 300° C. to 36.6% at 360° C. Like for γ-Al$_2$O$_3$, the selectivity to dimethyl sulfide was less than 5%.

Of all pure metal oxides, TiO$_2$ gave the highest selectivity for the formation of methyl mercaptan: 96% at 300° C., with decreasing selectivity at higher temperatures (S$_{DME,\ 360°\ C.}$=79.2%). In contrast to the other two metal oxides, the selectivity to dimethyl ether increased with increasing temperature, from S$_{DME,\ 300°\ C.}$=4.0% to S$_{DME,\ 360°\ C.}$=16.6%). Dimethyl sulfide was produced with a selectivity of less than 4%.

Compared to the pure metal oxide catalysts, all Cs loaded catalysts showed a dramatic increase in CH$_3$SH selectivity. For 10 wt.-% Cs on γ-Al$_2$O$_3$, the selectivity for the formation of CH$_3$SH increased to the range of from S$_{CH3SH,\ 300°\ C.}$=99.7% to S$_{CH3SH,\ 360°\ C.}$=98.3%. The selectivity to side product increased with increasing temperature: DME was formed with a selectivity of from S$_{DME,\ 300°\ C.}$=0.1% to S$_{DME,\ 360°\ C.}$=0.5%, and DMS was formed with a selectivity of from S$_{DMS,\ 300°\ C.}$=0.2% to S$_{DMS,\ 360°\ C.}$=1.2%. Further increase of the Cs loading to 20 wt.-% also increased the CH$_3$SH selectivity up to a selectivity of from S$_{CH3SH,\ 300°\ C.}$=99.9% to S$_{CH3SH,\ 360°\ C.}$=99.1%. In this case, the only side product found was DMS with a selectivity of from S$_{DMS,\ 300°\ C.}$=0.1% to S$_{DMS,\ 360°\ C.}$=0.9%.

For the ZrO$_2$ based catalysts, the selectivity to CH$_3$SH increased to a range of from S$_{CH3SH,\ 300°\ C.}$=99.9% to S$_{CH3SH,\ 360°\ C.}$=99.1%. Again, the only side found was DMS with a selectivity of from S$_{DMS,\ 300°\ C.}$=0.1% to S$_{DMS,\ 360°\ C.}$=0.9%. Increasing Cs loading to 20 wt.-% led to an even higher selectivity between S$_{CH3SH,\ 300°\ C.}$=99.9% and S$_{CH3SH,\ 360°\ C.}$=99.4%.

Similar results were found for the TiO$_2$ based catalysts: With 10 wt.-% Cs, the selectivity for CH$_3$SH increased to a range between S$_{CH3SH,\ 300°\ C.}$=99.9% to S$_{CH3SH,\ 360°\ C.}$=99.4%. Again, the only side found was dimethyl sulfide with a selectivity of from S$_{DMS,\ 300°\ C.}$=0.1% to S$_{DMS,\ 360°\ C.}$=0.6%. Increasing Cs loading to 20 wt.-% again led to an even higher selectivity between S$_{CH3SH,\ 300°\ C.}$=99.9% and S$_{CH3SH,\ 360°\ C.}$=99.5%.

TABLE 9

Summary of the product selectivities of the prepared catalysts (n.d. = not detectable)

| Catalyst | c(Cs) [wt.-%] | T [° C.] | S(CH$_3$SH) [%] | S(DME) [%] | S(DMS) [%] |
|---|---|---|---|---|---|
| γ-Al$_2$O$_3$ | — | 300 | 28.5 | 71.2 | <5 |
| | — | 360 | 71.2 | 28.6 | |
| | 10 | 300 | 99.7 | 0.1 | 0.2 |
| | 10 | 360 | 98.3 | 0.5 | 1.2 |
| | 20 | 300 | 99.9 | — | 0.1 |
| | 20 | 360 | 99.1 | — | 0.9 |
| ZrO2 | — | 300 | 53.1 | 46.7 | <5 |
| | — | 360 | 60 | 36.6 | |
| | 10 | 300 | 99.9 | — | 0.1 |
| | 10 | 360 | 99.1 | — | 0.9 |

TABLE 9-continued

Summary of the product selectivities of the prepared catalysts (n.d. = not detectable)

| Catalyst | c(Cs) [wt.-%] | T [° C.] | S(CH$_3$SH) [%] | S(DME) [%] | S(DMS) [%] |
|---|---|---|---|---|---|
| | 20 | 300 | 99.9 | — | n.d. |
| | 20 | 360 | 99.4 | — | n.d. |
| TiO2 | — | 300 | 96 | 4.0 | <4 |
| | — | 360 | 79.2 | 16.6 | |
| | 10 | 300 | 99.9 | — | 0.1 |
| | 10 | 360 | 99.4 | — | 0.6 |
| | 20 | 300 | 99.9 | — | n.d. |
| | 20 | 360 | 99.5 | — | n.d. |

4. Comparative Examples

Comparative examples were carried out with a catalyst comprising Cs$_2$WS$_4$ on γ-Al$_2$O$_3$. Said catalyst was prepared by two-step incipient wetness impregnation process. First, 5.0 g γ-Al$_2$O$_3$ (analogue to SPH 509 Axens, grain size of 150-250 μm) were impregnated with 0.64 g of cesium acetate (Sigma Aldrich, >99.99%) dissolved in 1.6 mL of H$_2$O. The sample was dried at room temperature overnight to give Cs/Al$_2$O$_3$. Next, the Cs$_2$WS$_4$/Al$_2$O$_3$ system was synthesized as followed: Cs$_2$WS$_4$ crystals were formed by precipitation, mixing a solution of 350 mg of (NH$_4$)$_2$WS$_4$ in 20 ml of H$_2$O and 325 mg of Cs$_2$CO$_3$ in 20 ml of H$_2$O. A yellow precipitate was formed. These solids were filtered, washed with ice-cold water and 1-propanol. Due to the low solubility of Cs$_2$WS$_4$, 450 mg of these were dissolved in 150 ml of water. Then 2 g of Cs/Al$_2$O$_3$ were added to the solution. The water was removed by evaporation in continuous rotation, precipitating the Cs$_2$WS$_4$ crystals on the solid sample. The sample was dried at room temperature overnight. After drying, the sample was calcined at 455° C. for 4 h, with an increment of 5° C./min. The prepared catalyst had a tungsten content of 5.1 wt.-%, a cesium content of 20.6 wt.-%, a pore volume of 0.20 cm$^3$ g$^{-1}$, and a BET surface area of 141 m$^2$ g$^{-1}$, both measured as described above. Adsorption followed by temperature programmed desorption of H$_2$S was performed with a pulse technique using a flow apparatus equipped with a mass spectrometer (QME 200, Pfeiffer Vacuum). A sample of catalyst was loaded in a quartz reactor and activated in situ under 4.2 vol.-% H$_2$S/He with a flow of 6 ml/min at 360° C. for 2 h. For H$_2$S adsorption, the temperature was set to 360° C. and the sample was flushed with He for 1 hour prior to adsorption. Pulses of 4.4 vol.-% of H$_2$S in He were introduced every 30 min (5.0 μmol/min of H$_2$S). The total concentration of gas adsorbed was calculated as the sum of the uptakes per pulse.

The thus obtained catalyst was tested under the same reaction condition and the same reaction tube as in example 3. Prior to testing, the catalyst was activated by treatment in H$_2$S with a flow rate of 20 ml/min at 360° C. for 2 hours.

The MeOH conversion, yields for CH$_3$SH, DME, and DMS and the selectivities for CH$_3$SH, DME and DMS at temperatures of 300, 320, 340 and 360° C. are summarized in Table 10.

TABLE 10

Summary of the results of the comparative examples

| T [° C.] | X(CH$_3$OH) [%] | Y(CH$_3$SH) [%] | Y(DME) [%] | Y(DMS) [%] | S(CH$_3$SH) [%] | S(DME) [%] | S(DMS) [%] |
|---|---|---|---|---|---|---|---|
| 300 | 10.8 | 10.8 | 0.00 | 0.00 | 100.0 | 0.0 | 0.0 |
| 320 | 17.4 | 17.4 | 0.00 | 0.02 | 100.0 | 0.0 | 0.1 |

TABLE 10-continued

Summary of the results of the comparative examples

| T [° C.] | X(CH$_3$OH) [%] | Y(CH$_3$SH) [%] | Y(DME) [%] | Y(DMS) [%] | S(CH$_3$SH) [%] | S(DME) [%] | S(DMS) [%] |
|---|---|---|---|---|---|---|---|
| 340 | 28.4 | 28.3 | 0.01 | 0.10 | 99.6 | 0.0 | 0.4 |
| 360 | 44.3 | 44.0 | 0.03 | 0.20 | 99.3 | 0.1 | 0.5 |

Figure 15:
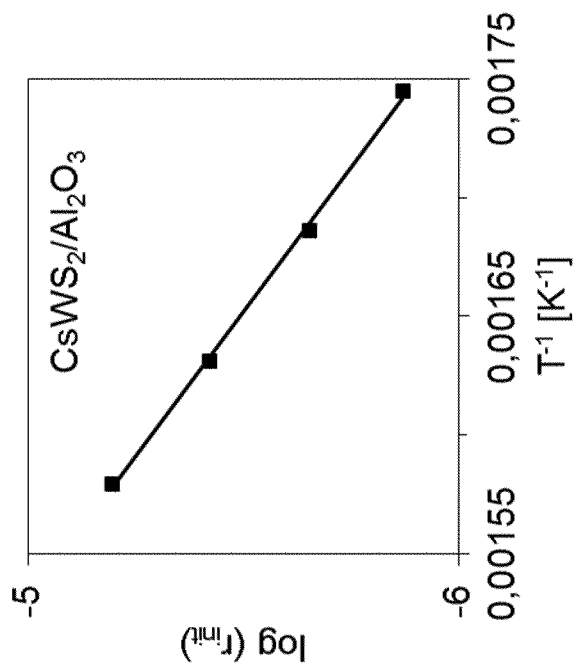
FIG. 15 shows the initial rates for methyl mercaptan formation over γ-$Al_2O_3$ loaded with $CsWS_2$ (tungsten content of 5.1 wt.-%, and cesium content of 20.6 wt.-%) at temperatures of 300, 320, 340 and 360° C. (solid squares).

Initial rates for CH$_3$SH formation are shown in FIG. 15. The highest rate in methanol thiolation was observed at a temperature of 300° C. ($1.34 \cdot 10^{-6}$ mol$_{CH3SH}$ s$^{-1}$ g$_{cat}^{-1}$), with following rates at higher temperatures and the lowest rate at a temperature of 360° C. ($6.38 \cdot 10^{-6}$ mol$_{CH3SH}$ s$^{-1}$ g$_{cat}^{-1}$).

The invention claimed is:

1. A process for preparing an alkyl mercaptan, the process comprising:
   reacting an alkyl alcohol with hydrogen sulfide in the presence of a catalyst comprising:
   a support; and
   5 to 20 wt. % of cesium oxide, based on total catalyst weight, wherein the support consists of titanium dioxide and/or zirconium dioxide, and at least a part of the support has a tetragonal phase.

2. The process of claim 1, wherein the catalyst is a full catalyst.

3. The process of claim 1, wherein the catalyst is a core-shell catalyst.

4. The process of claim 1, wherein the catalyst is obtained by a process comprising:

(a) impregnating a support consisting of titanium dioxide and/or zirconium dioxide with an aqueous solution comprising a soluble cesium compound, to obtain an impregnated support;
   (b) drying the impregnated support, to obtain a dried impregnated support; and
   (c) calcining the dried impregnated support to provide the catalyst.

5. The process of claim 4, wherein the impregnating (a), the drying (b), and the calcining (c) are repeated at least once.

6. The process of claim 4, wherein the process to obtain the catalyst further comprises:
   (d1) shaping the catalyst obtained from the calcining (c) to give a full catalyst.

7. The process of claim 4, wherein the process to obtain the catalyst further comprises:
   d2) applying the catalyst obtained from the calcining (c) to a core to provide a core-shell catalyst.

8. The process of claim 1, wherein the alkyl alcohol to be reacted is methanol and the alkyl mercaptan to be prepared is methyl mercaptan.

* * * * *